United States Patent
Meadows et al.

(10) Patent No.: US 8,960,013 B2
(45) Date of Patent: Feb. 24, 2015

(54) CEMENT TESTING

(75) Inventors: David Leon Meadows, Marlow, OK (US); Robert Phillip Darbe, Tomball, TX (US); Walmy Cuello Jimenez, Houston, TX (US); Robert Lee Browning, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 235 days.

(21) Appl. No.: 13/409,745

(22) Filed: Mar. 1, 2012

(65) Prior Publication Data

US 2013/0228019 A1     Sep. 5, 2013

(51) Int. Cl.
    *G01N 3/08*     (2006.01)
(52) U.S. Cl.
    USPC .......................................................... 73/803
(58) Field of Classification Search
    USPC ................................................... 73/821, 803
    See application file for complete search history.

(56) References Cited

U.S. PATENT DOCUMENTS

| | | |
|---|---|---|
| 2,662,827 A | 12/1953 | Clark |
| 3,541,845 A | 11/1970 | Kierkegaard-Hansen |
| 3,574,281 A | 4/1971 | Casey et al. |
| 3,619,463 A | 11/1971 | Budin et al. |
| 3,779,085 A | 12/1973 | Rice |
| 4,138,892 A | 2/1979 | Davis |
| 4,182,191 A | 1/1980 | Ikeda |
| 4,259,868 A | 4/1981 | Rao et al. |
| 4,377,087 A | 3/1983 | Rodot |
| 4,389,896 A | 6/1983 | Babcock |
| 4,408,489 A | 10/1983 | Spangle |
| 4,430,889 A | 2/1984 | Sutton |
| 4,487,056 A | 12/1984 | Wiley |
| 4,491,017 A | 1/1985 | Iyer |
| 4,538,452 A | 9/1985 | Hrvojic |
| 4,567,759 A | 2/1986 | Ekstrom et al. |
| 4,567,765 A | 2/1986 | Rao et al. |
| 4,573,342 A | 3/1986 | Jones |
| 4,607,530 A | 8/1986 | Chow |
| 4,648,264 A | 3/1987 | Freese et al. |
| 4,685,092 A | 8/1987 | Dumont |
| 4,691,558 A | 9/1987 | Vinson et al. |
| 4,703,427 A | 10/1987 | Catala et al. |
| 4,757,479 A | 7/1988 | Masson et al. |
| 4,809,237 A | 2/1989 | Vogel et al. |

(Continued)

FOREIGN PATENT DOCUMENTS

| | | |
|---|---|---|
| DE | 86 01 833 | 1/1987 |
| EP | 0 124 383 A1 | 11/1984 |

(Continued)

OTHER PUBLICATIONS

Authorized officer Athina Nickitas-Etienne, International Preliminary Report on Patentability in International application No. PCT/GB2010/002001, mailed Dec. 6, 2012, 7 pages.

(Continued)

*Primary Examiner* — John Fitzgerald
(74) *Attorney, Agent, or Firm* — John W. Wustenberg; Fish & Richardson P.C.

(57) ABSTRACT

Systems and methods provide for testing a cement by applying force in a first direction until the first portion of the cement sample fails in compression or tension; and applying force a second direction opposite the first direction until the second portion of the cement sample fails in tension or compression.

18 Claims, 11 Drawing Sheets

(56) References Cited

U.S. PATENT DOCUMENTS

| | | | |
|---|---|---|---|
| 4,823,594 A | 4/1989 | Gray | |
| 4,848,145 A | 7/1989 | Blaschke et al. | |
| 4,893,285 A | 1/1990 | Masson et al. | |
| 4,896,303 A | 1/1990 | Leslie et al. | |
| 4,970,695 A | 11/1990 | Huau | |
| 5,009,512 A | 4/1991 | Lessi et al. | |
| 5,036,709 A | 8/1991 | McRae | |
| 5,089,989 A | 2/1992 | Schmidt et al. | |
| 5,127,473 A | 7/1992 | Harris et al. | |
| 5,159,828 A | 11/1992 | Steiger et al. | |
| 5,216,638 A | 6/1993 | Wright | |
| 5,226,310 A | 7/1993 | Steiger | |
| 5,233,863 A | 8/1993 | Surjaatmadja et al. | |
| 5,248,200 A | 9/1993 | Walsh | |
| 5,325,723 A | 7/1994 | Meadows et al. | |
| 5,346,012 A | 9/1994 | Heathman et al. | |
| 5,353,637 A | 10/1994 | Plumb et al. | |
| 5,368,103 A | 11/1994 | Heathman et al. | |
| 5,377,160 A | 12/1994 | Tello et al. | |
| 5,377,753 A | 1/1995 | Haberman et al. | |
| 5,389,706 A | 2/1995 | Heathman et al. | |
| 5,412,990 A | 5/1995 | D'Angelo et al. | |
| 5,487,307 A | 1/1996 | Landgren et al. | |
| 5,488,994 A | 2/1996 | Laurel et al. | |
| 5,544,704 A | 8/1996 | Laurel et al. | |
| 5,571,951 A | 11/1996 | Jamth | |
| 5,572,021 A | 11/1996 | Heathman et al. | |
| 5,696,059 A | 12/1997 | Onan et al. | |
| 5,712,431 A | 1/1998 | Vilendrer | |
| 5,718,292 A | 2/1998 | Heathman et al. | |
| 5,741,971 A | 4/1998 | Lacy | |
| 5,763,773 A | 6/1998 | Birchak et al. | |
| 5,783,822 A | 7/1998 | Buchanan et al. | |
| 5,787,983 A | 8/1998 | Heathman et al. | |
| 5,836,200 A | 11/1998 | Belonenko et al. | |
| 5,869,750 A | 2/1999 | Onan et al. | |
| 5,964,293 A | 10/1999 | Chatterji et al. | |
| 5,968,255 A | 10/1999 | Mehta et al. | |
| 5,969,059 A | 10/1999 | Murai et al. | |
| 5,972,103 A | 10/1999 | Mehta et al. | |
| 5,992,223 A | 11/1999 | Sabrins et al. | |
| 5,996,693 A | 12/1999 | Heathman | |
| 6,019,835 A | 2/2000 | Chatterji et al. | |
| 6,053,245 A | 4/2000 | Haberman | |
| 6,055,874 A | 5/2000 | Onan et al. | |
| 6,060,434 A | 5/2000 | Sweatman et al. | |
| 6,070,662 A | 6/2000 | Ciglenec et al. | |
| 6,112,599 A | 9/2000 | Maki, Jr. | |
| 6,124,246 A | 9/2000 | Heathman et al. | |
| 6,134,954 A | 10/2000 | Suresh et al. | |
| H1932 H | 1/2001 | Heathman et al. | |
| 6,170,575 B1 | 1/2001 | Reddy et al. | |
| 6,209,646 B1 | 4/2001 | Reddy et al. | |
| 6,227,039 B1 | 5/2001 | Te'eni | |
| 6,227,294 B1 | 5/2001 | Chatterji et al. | |
| 6,245,142 B1 | 6/2001 | Reddy et al. | |
| 6,258,757 B1 | 7/2001 | Sweatman et al. | |
| 6,269,684 B1 | 8/2001 | Maki, Jr. et al. | |
| 6,270,565 B1 | 8/2001 | Heathman | |
| 6,345,535 B1 | 2/2002 | Sabins et al. | |
| 6,367,549 B1 | 4/2002 | Chatterji et al. | |
| 6,367,550 B1 | 4/2002 | Chatterji et al. | |
| 6,379,456 B1 | 4/2002 | Heathman et al. | |
| 6,444,316 B1 | 9/2002 | Reddy et al. | |
| 6,454,001 B1 | 9/2002 | Thompson et al. | |
| 6,478,868 B1 | 11/2002 | Reddy et al. | |
| 6,478,869 B2 | 11/2002 | Reddy et al. | |
| 6,484,568 B1 | 11/2002 | Griffith et al. | |
| 6,494,951 B1 | 12/2002 | Reddy et al. | |
| 6,510,743 B2 | 1/2003 | McAfee et al. | |
| 6,527,051 B1 | 3/2003 | Reddy et al. | |
| 6,527,438 B2 | 3/2003 | Zollinger et al. | |
| 6,547,871 B2 | 4/2003 | Chatterji et al. | |
| 6,554,071 B1 | 4/2003 | Reddy et al. | |
| 6,591,910 B1 | 7/2003 | Chatterji et al. | |
| 6,595,068 B2 | 7/2003 | Brovold et al. | |
| 6,610,139 B2 | 8/2003 | Reddy et al. | |
| 6,644,402 B1 | 11/2003 | Sharma et al. | |
| 6,655,213 B1 | 12/2003 | Reinhardt et al. | |
| 6,660,080 B2 | 12/2003 | Reddy et al. | |
| 6,711,941 B2 | 3/2004 | Braithwaite et al. | |
| 6,762,156 B2 | 7/2004 | Heathman et al. | |
| 6,767,867 B2 | 7/2004 | Chatterji et al. | |
| 6,782,735 B2 | 8/2004 | Walters et al. | |
| 6,789,621 B2 | 9/2004 | Wetzel et al. | |
| 6,797,054 B2 | 9/2004 | Chatterji et al. | |
| 6,817,238 B2 | 11/2004 | Go Boncan et al. | |
| 6,818,596 B1 | 11/2004 | Hayes | |
| 6,828,922 B1 | 12/2004 | Gremmert et al. | |
| 6,829,922 B2 | 12/2004 | Patin et al. | |
| 6,834,233 B2 | 12/2004 | Economides et al. | |
| 6,843,846 B2 | 1/2005 | Chatterji et al. | |
| 6,874,353 B2 | 4/2005 | Johnson et al. | |
| 6,892,814 B2 | 5/2005 | Heathman et al. | |
| 6,910,535 B2 | 6/2005 | Tare et al. | |
| 6,918,292 B2 | 7/2005 | Go Boncan et al. | |
| 6,951,249 B1 | 10/2005 | Chatterji et al. | |
| 6,964,302 B2 | 11/2005 | Luke et al. | |
| 6,978,835 B1 | 12/2005 | Reddy et al. | |
| 6,994,164 B2 | 2/2006 | Tare et al. | |
| 7,004,256 B1 | 2/2006 | Chatterji et al. | |
| 7,008,477 B2 | 3/2006 | Chatterji et al. | |
| 7,013,975 B2 | 3/2006 | Chatterji et al. | |
| 7,048,054 B2 | 5/2006 | Heathman et al. | |
| 7,089,816 B2 * | 8/2006 | Hakimuddin | 73/866 |
| 7,096,944 B2 | 8/2006 | Vargo, Jr. et al. | |
| 7,128,142 B2 | 10/2006 | Heathman et al. | |
| 7,128,149 B2 | 10/2006 | Heathman et al. | |
| 7,143,827 B2 | 12/2006 | Chatterji et al. | |
| 7,178,590 B2 | 2/2007 | Vargo, Jr. et al. | |
| 7,191,663 B2 | 3/2007 | Go Boncan et al. | |
| 7,222,676 B2 | 5/2007 | Patel et al. | |
| 7,240,545 B1 | 7/2007 | Jennings | |
| 7,244,303 B2 | 7/2007 | Chatterji et al. | |
| 7,255,170 B2 | 8/2007 | Chatterji et al. | |
| 7,284,898 B2 | 10/2007 | Duell et al. | |
| 7,285,166 B2 | 10/2007 | Luke et al. | |
| 7,296,927 B2 * | 11/2007 | Reddy et al. | 374/47 |
| 7,325,629 B2 | 2/2008 | Blaschke et al. | |
| 7,373,982 B2 | 5/2008 | Brothers et al. | |
| 7,380,466 B2 | 6/2008 | Deeg | |
| 7,549,320 B2 | 6/2009 | Funkhouser et al. | |
| 7,552,648 B2 | 6/2009 | McMechan et al. | |
| 7,621,186 B2 * | 11/2009 | Heathman et al. | 73/803 |
| 2001/0001381 A1 | 5/2001 | Reddy et al. | |
| 2001/0037687 A1 | 11/2001 | Brovold et al. | |
| 2003/0140707 A1 | 7/2003 | Pyle et al. | |
| 2003/0150263 A1 | 8/2003 | Economides et al. | |
| 2003/0161211 A1 | 8/2003 | Duell et al. | |
| 2003/0221829 A1 | 12/2003 | Patel et al. | |
| 2004/0054262 A1 | 3/2004 | Horak | |
| 2004/0055392 A1 | 3/2004 | Patin et al. | |
| 2004/0154263 A1 | 8/2004 | Li et al. | |
| 2004/0221990 A1 | 11/2004 | Heathman et al. | |
| 2004/0226483 A1 | 11/2004 | Chatterji et al. | |
| 2005/0009710 A1 | 1/2005 | Heathman et al. | |
| 2005/0080161 A1 | 4/2005 | Tare et al. | |
| 2005/0109507 A1 | 5/2005 | Heathman et al. | |
| 2005/0126300 A1 | 6/2005 | Go Boncan et al. | |
| 2005/0135185 A1 | 6/2005 | Duell et al. | |
| 2005/0152432 A1 | 7/2005 | Hakimuddin | |
| 2005/0204960 A1 | 9/2005 | Heathman et al. | |
| 2006/0000612 A1 | 1/2006 | Reddy et al. | |
| 2006/0225523 A1 | 10/2006 | Reddy et al. | |
| 2006/0258545 A1 | 11/2006 | Chatterji et al. | |
| 2007/0012441 A1 | 1/2007 | Heathman et al. | |
| 2007/0056383 A1 | 3/2007 | Deeg | |
| 2007/0082822 A1 | 4/2007 | Kirsner et al. | |
| 2007/0105995 A1 | 5/2007 | Chatterji et al. | |
| 2007/0169937 A1 | 7/2007 | Allin et al. | |
| 2007/0173412 A1 | 7/2007 | Allin et al. | |
| 2008/0168848 A1 * | 7/2008 | Funkhouser et al. | 73/865.6 |
| 2008/0178683 A1 * | 7/2008 | Heathman et al. | 73/803 |
| 2008/0197605 A1 | 8/2008 | Blaschke et al. | |

(56) References Cited

U.S. PATENT DOCUMENTS

| | | | |
|---|---|---|---|
| 2009/0084189 | A1 | 4/2009 | McMechan et al. |
| 2011/0061525 | A1* | 3/2011 | Gray et al. .................. 92/75 |
| 2011/0094295 | A1* | 4/2011 | Meadows et al. ............ 73/38 |

FOREIGN PATENT DOCUMENTS

| | | |
|---|---|---|
| EP | 0 176 400 B1 | 4/1986 |
| EP | 0 101 580 B1 | 12/1986 |
| EP | 0 110 750 B1 | 9/1988 |
| EP | 0 098 778 B1 | 3/1989 |
| EP | 0 198 985 B1 | 12/1989 |
| EP | 0 443 936 A1 | 8/1991 |
| EP | 0 395 499 B1 | 7/1993 |
| EP | 0 176 408 B1 | 4/1996 |
| EP | 1 189 051 | 2/2001 |
| EP | 0 865 612 B1 | 6/2002 |
| EP | 1 541 987 | 6/2005 |
| FR | 2 340 551 | 9/1977 |
| FR | 2 746 920 | 10/1997 |
| FR | 2 965 925 | 4/2012 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/008302 A1 | 10/2004 |
| WO | WO 2005/065411 | 7/2005 |
| WO | WO 2008/084201 | 7/2008 |
| WO | WO 2010/094925 | 8/2010 |

OTHER PUBLICATIONS

International Search Report and Written Opinion in International Application No. PCT/US2013/024879, mailed May 27, 2013, 11 pages.

Deeg, Wolfgang, et al., "How Foamed Cement Advantages Extend to Hydraulic Fracturing Operations," World Oil, Nov. 1999, pp. 51-53.

Dillenbeck, R.L., GoBoncan, V., and Rogers, M.J., "Testing Cement Static Tensile Behavior Under Downhole Conditions," SPE 97967, Society of Petroleum Engineers, Copyright 2005, 12 pages.

FlexiForce®, materials downloaded from Tekscan website (www.tekscan.com) on FlexiForce® sensors), http://www.tekscan.com/flexiforce.html, visited Aug. 3, 2005, 20 pages.

Goodwin, K.J., "Cement Sheath Stress Failure," SPE Drilling Engineering, SPE 20453, Dec. 1992, pp. 291-296, and additional pp. 501-508 from SPE 20453.

Love, A.E.H., "A Treatise on the Mathematical Theory of Elasticity," Fourth Edition, Dover Publications, New York, 1944, pp. 144-145.

Minear, John W. and Goodwin, K. Joe, "Cement-Sheath Evaluation," Chapter 10, Petroleum Well Construction, John Wiley & Sons Publisher, ISBN 0-471-96938-9, copyright 1998, front and back cover and pp. 271-296.

Thiercelin, J.J., et al., "Cement Design Based on Cement Mechanical Response," SPE Drilling & Completion, Society of Petroleum Engineers, SPE 52890, Dec. 1998, pp. 266-273.

"Standard Test Method for Tensile Strength of Hydraulic Cement Mortars", ASTM Standards, C-190-85, pp. 197-202.

Clayton, N. et al., "The Diphase Concept, With Particular Reference to Concrete", Developments in Concrete Technology, vol. 1, F. D. Lydon, Ed.; Applied Science Publisher Ltd, Chapter 7, pp. 283-318, (1979).

Clayton, N., "Fluid-pressure Testing of Concrete Cylinders," Magazine of Concrete Research, vol. 30, No. 102, pp. 26-30, (1978).

Mindess, S. et al., "The Nitrogen Gas Tension Test of Concrete", Proceedings of ConMat '05 and Mindess Symposium, Aug. 22-24, 2005, The University of British Columbia, Vancouver, Canada, 8 pages, (2005).

Richart, Frank E. et al., "A Study of the Failure of Concrete Under Combined Compressive Stresses", The University of Illinois—Engineering Experiment Station, Bulletin No. 185, pp. 3-253, (1928).

Sabins, Fred, "MMS Project Long-Term Integrity of Deepwater Cement Systems Under Stress/Compaction Conditions", CSI Technologies, Sep. 3, 2004.

Gary Funkhouser et al., "Measuring Cement Properties" U.S. Appl. No. 11/622,255, filed Jan. 11, 2007 (25 pages).

Wolfgang F. J. Deeg, "Apparatus and Method for Determining Mechanical Properties of Cement for a Well Bore" U.S. Appl. No. 11/206,719, filed Aug. 18, 2005 (32 pages).

David Leon Meadows et al., "Cement Testing" U.S. Appl. No. 12/607,560, filed Oct. 28, 2009 (33 pages).

David Leon Meadows et al., "Cement Testing" U.S. Appl. No. 13/542,011, filed Jul. 5, 2012 (31 pages).

Authorized Officer Philippe Becamel, PCT International Preliminary Report on Patentability, PCT/US2013/024879, Sep. 12, 2014, 7 pages.

Bridgman, P.W., "V. Breaking Tests Under Hydrostatic Pressure and Conditions of Rupture", Philosophical Magazine and Journal of Science, vol. 24, Sixth Series, pp. 63-80, (1912).

* cited by examiner

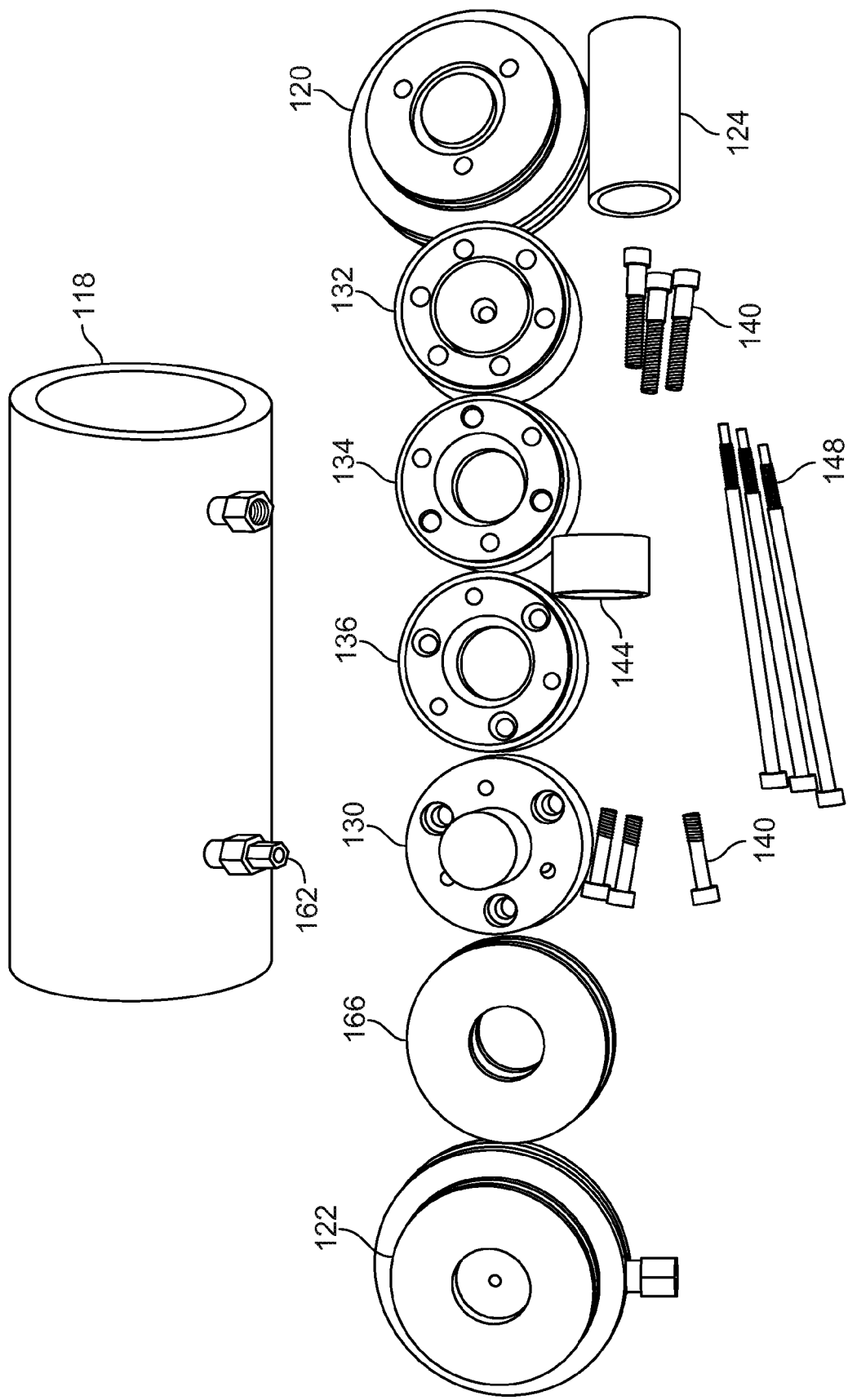

CEMENT TESTING

TECHNICAL FIELD

This disclosure relates to measuring mechanical properties.

BACKGROUND

Some well bores, for example some oil and gas wells, are lined with a casing. The cemented casing stabilizes the sides of the well bore, prevents fluids (liquids or gases) in the well bore from entering the surrounding earth formations, and/or prevents fluids from zones other than the producing zones from entering the well bore.

In a typical cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above or below ambient temperature and/or above ambient pressure. In designing a cement formulation, a number of potential mixtures may be evaluated to determine their mechanical properties under various conditions.

SUMMARY

Using the devices and methods described, mechanical properties of a cement sample can be measured under both compression and tension in simulated downhole conditions. The cement samples can be cured at downhole conditions and then tested at desired intervals in the hydration process. The curing or cured samples can be subjected to tests including direct pull tensile strength tests and compressive strength tests without removal from the pressure vessel being used to maintain downhole conditions. This enables the application of drained or undrained unconfined compressive testing conditions, drained or undrained confined compressive testing conditions, drained or undrained unconfined tensile testing conditions, and drained or undrained confined tensile testing conditions as well as hydrostatic test conditions and derivatives. The devices and methods described allow for the determination of the stress-strain relationship under both uniaxial and triaxial loading in addition to the uniaxial and triaxial failure limits as reflected in various characteristic cement values such as, for example, Poison's Ratio, Modulus of Elasticity, Bulk Modulus, tensile and compression yield and strength, cohesion, and friction angle.

In some aspects, systems for testing a cement sample include: at least one cement testing apparatus, each cement testing apparatus comprising: a sample container having wall segments defining a first interior volume, a second interior volume, and an aperture extending between the first sample volume and the second sample volume; and a piston connected to the sample container; wherein the wall segments are connected to each other such that movement of the piston in a first direction applies compression to a portion of the cement sample in the first interior volume and movement of the piston in a second direction opposite the first direction applies tension to a portion of the cement sample in the second interior volume.

In some aspects, devices for testing cement include: a sample container having a flexible tubular member defining a first interior volume and a plurality of tension members defining a second interior volume, the sample container defining an aperture extending between the first sample volume and the second sample volume; and a piston connected to the sample container; wherein the wall segments are connected to each other such that movement of the piston in a first direction applies compression to a portion of the cement sample in the first interior volume and movement of the piston in a second direction opposite the first direction applies tension to a portion of the cement sample in the second interior volume.

Embodiments can include one or more of the following features.

The flexible tubular member can include a rubber sleeve or could be formed from high temperature elastomers or high temperature polymers.

In some embodiments, the wall segments comprise a first tension member and a second tension member adjacent the first tension member, the second tension member disposed between the piston and first tension member such that movement of the piston in the first direction presses the second tension member towards the first tension member and movement of the piston in the second direction pulls the second tension member away from the first tension member. In some cases, devices include a first attachment member engaging the first tension member to limit movement of the first tension member towards the piston. Other implementations may use a mechanical offset that is part of the cell wall engineered to limit the movement of the first tension member as well. The first attachment member can be an elongated member fixed in position relative to an end wall of the sample container opposite the piston, the elongated member extending through a bore defined in first tension member. In some cases, the elongated member comprises a flanged head and the second tension member defines a recess aligned with and sized to receive the flanged head of the elongated member. The second tension member can be attached to the piston.

In some cases, a transverse cross-section of the second interior volume taken at an intersection between the first tension member and the second tension member is smaller than at least one transverse cross-section of the second interior volume taken at a location within the first tension member and at least one transverse cross-section of the second interior volume taken at a location within the second tension member. In some cases, devices include a flexible tubular member disposed in a recess defined by in the first tension member and the second tension member.

In some embodiments, at least one wall segment defining the first interior volume of the sample container is formed of a material that does not significantly increase resistance to compression of the portion of the cement sample in the first interior volume of the sample container. In some cases, the at least one wall segment defining the first interior volume of the sample container comprises a flexible tubular member. Examples of flexible tubular members comprise rubber sleeves, or other high temperature elastomers or polymers.

In some embodiments, the system further comprises a pressure vessel containing the sample container. In some cases, an interior surface of the pressure vessel partially defines the first interior volume of the sample container or the second interior volume of the sample container.

In some embodiments, the portion of the cement sample in the first interior volume and the portion of the cement sample in the second interior volume are axially aligned. In some cases, the plurality of tension members comprise a first tension member and a second tension member adjacent the first tension member, the second tension member disposed between the piston and first tension member such that movement of the piston in the first direction presses the second tension member towards the first tension member and movement of the piston in the second direction pulls the second tension member away from the first tension member. In some cases, devices include an elongated member fixed in position relative to an end wall of the sample container opposite the piston, the elongated member extending through a bore defined in first tension member to limit movement of the first tension member towards the piston. Other implementations may use a mechanical offset that is part of the cell wall engineered to limit the movement of the first tension member as well.

In some aspects, methods of testing cement (e.g., cement samples/specimens) include: forming a cement sample with a first portion axially aligned with a second portion; moving a piston in a first direction until the first portion of the cement sample fails in compression; and moving the piston in a second direction opposite the first direction until the second portion of the cement sample fails in tension. Either compression or tensile testing can be performed first having no effects on the tests results. Moreover, sample integrity of either portion of the sample can be maintained while running either test. Embodiments can include one or more of the following features.

In some embodiments, methods also include: mixing a slurry of the cement sample at pressure and/or temperature conditions that are different than ambient conditions; and transferring the slurry of the cement sample to the sample container for curing without exposure to ambient conditions.

In some embodiments, methods also include: curing a cement sample at first pressure conditions that are different than ambient conditions; and pulling on ends of the sample to apply axial tension to the sample while maintaining the sample at the first pressure conditions.

In some embodiments, moving the piston in a second direction opposite the first direction until the second portion of the cement sample fails in tension occurs after moving a piston in a first direction until the first portion of the cement sample fails in compression. In some embodiments, moving the piston in a second direction opposite the first direction until the second portion of the cement sample fails in tension occurs before moving a piston in a first direction until the first portion of the cement sample fails in compression.

In some embodiments, methods also include: simultaneously setting initial pressure and/or temperature conditions in multiple testing apparatuses; isolating at least one of the testing apparatuses from others of the multiple testing apparatuses; and testing a mechanical property of cement sample(s) in the at least one of the testing apparatuses isolated from others of the multiple testing apparatuses. In some cases, methods also include: calculating a failure mode for the cement being tested based on testing a mechanical property of the cement sample in each of the multiple testing apparatuses. Running a specific test (e.g., with the same pressure and temperature conditions) on multiple testing devices can allow for statistical analyses on the resulting measured properties. Running multiple tests (e.g., with different pressure and temperature conditions) on multiple testing devices can allow for performance evaluation of the cement system. There is also the potential of evaluating different cement systems simultaneously.

The methods and systems described can provide one or more of the following advantages.

The methods and systems described can allow a liquid slurry to cure at pressure and temperature conditions and, while curing or after cured, to be tested for volume changes, the mechanical response of the sample, and failure limits without removing curing, or cured, cement from the testing apparatus. Testing in the curing vessel can reduce the possibility that removal of the sample from the testing apparatus could impart damage to the sample that would influence subsequent results. Testing in the curing vessel can also save time and money, and reduces the limits on the ability to test curing in a small time window relative to cure associated with systems which require removal of the curing vessel for testing. Moreover, tensile and compressive samples can be cured simultaneously in the same apparatus; both compressive and tensile testing can take place on the same testing apparatus as well.

The methods and systems described can allow for independent control over pore pressure, confining pressure, and load magnitude, direction, and rate. In combination, the independent control of these parameters allows for multiple samples to be tested in replicate and with changes to one parameter at a time to provide statistics as well as different testing conditions.

The methods and systems described can provide the ability to cure and test cement at conditions that represent a cemented well casing.

The devices and methods described incorporate a specially designed pressure chamber along with various highly functional parts which allows for testing both compression and tension in the same cell without changing components. Flexible tubular members (e.g., rubber sleeves) along the same cell allow for sample molding while keeping the same specimen's shape during the initial hydration stage. The flexible tubular members offer negligible resistance during testing. A hydraulic piston allows the application of axial stress on the cement samples. In some embodiments, the same functionality is provided by employing power screws, linear actuators, load frames, etc. The cell is configured to cause different portions of a single sample to fail in compression and in tension without rearranging any mechanical parts, which will result in substantially reduced sample preparation and specimens test time.

The details of one or more embodiments are set forth in the accompanying drawings and the description below.

DESCRIPTION OF DRAWINGS

FIG. 1F shows the disassembled components of the cement testing apparatus of FIGS. 1A-1E.

Like reference symbols in the various drawings indicate like elements.

DETAILED DESCRIPTION

Figure 1A:
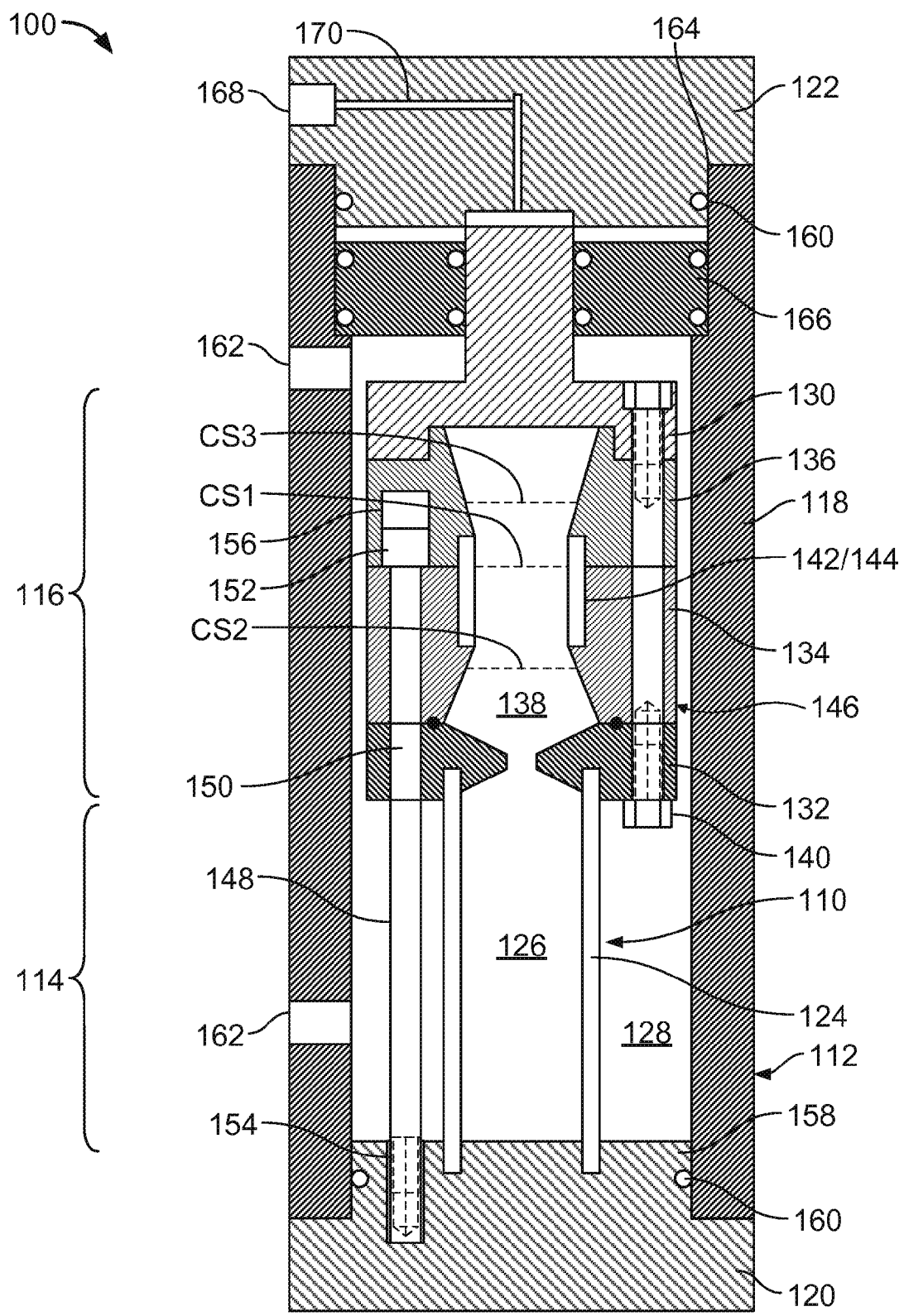
FIGS. 1A-1C are cross-sections of a cement testing apparatus.
Figure 1B:
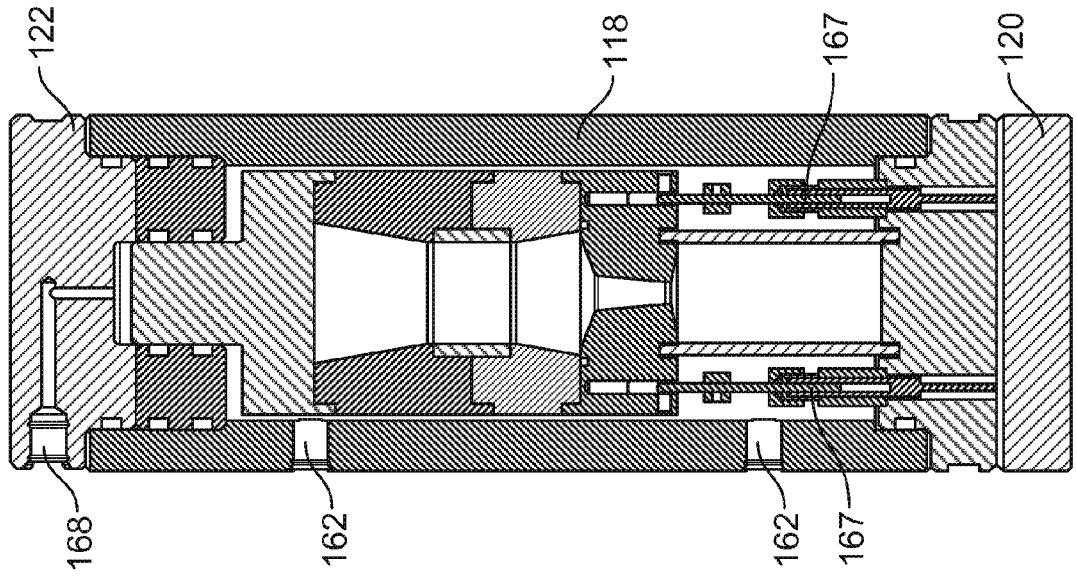

The described devices and methods incorporate a specially designed pressure chamber along with various highly functional parts which allows for testing both compression and tension in the same cell without changing components. Flexible tubular members, for both tension and compression, along the same cell allow for sample molding while keeping the same specimen shape during the initial hydration stage. The Flexible tubular members offer negligible resistance during testing. Axial stresses can be applied to cement samples using a device such as, for example, a hydraulic piston, linear actuator, or a power screw. Confinement/radial stress can be applied to samples using a pressure fluid that is directly applied to the sample (e. g., pressure fluid controlled by an external pressure source such as a pump or pumps). The cell is configured to cause different portions of a single sample to fail in compression and in tension without rearranging any mechanical parts, which can result in substantially reduced sample preparation and test time.

These devices and methods can allow an accurate measurement of mechanical properties and behaviors of cement formulations including, for example, tensile strength, compressive strength, shrinkage, and other properties. For example, a sample cement composition can be cured or partially cured at downhole conditions (e.g., temperatures may range from extremely cold or below ambient temperatures up to substantially higher anticipated bottomhole conditions and pressures may be within ambient conditions up to for instance 60,000 psi or greater) while monitoring chemical and bulk shrinkage and, at a specified time, changing the stress conditions applied to the sample while monitoring the mechanical response until failure occurs or until certain stress level is reached. Mechanical properties of the cement sample can be calculated, in some cases, based on the response of the sample to the differential stress conditions while the failure limits established by the material response or maximum stress endured before failure. In some cases, cyclic testing is performed to determine other properties of the cement such as, endurance limit or remaining capacity of the cement to withstand cyclic loading that simulates well operations procedures such as, for example, lifting, stimulation, fracturing, pressure test. Cyclic testing takes into account that the cement sheath for oil well applications should be designed considering its integrity not only during the early stages of the construction of the well but also during the prolonged life of the well simulating well operations (e.g., cement hydration, hydraulic stimulation, hydrocarbon production, fluid injection, gas lift, etc.). Therefore, determining the capacity of a cement to withstand cyclic stresses, which can be accomplished by performing cyclic test at various load levels (this is also known as the endurance limit or remaining capacity of the cement) can be a key parameter in developing a cement formulation that can provide safe, economic and continuous production.

As used herein, "cement" and "cement composition" encompass a fluid mixture that hardens into a solid, and may be any agent suitable to bond casing or other elements (e.g. tubulars) to well bore walls or to other tubing used for downhole applications. Some examples of cement include hydraulic cement (e.g., Portland cement formulations), non-hydraulic cement (e.g., polymer resin formulations), and mixtures thereof having, for instance, silica, Pozzolans, cross-linked polymers, ceramics, among other components. As used herein, "curing" refers to the reactions through which cement hardens from a fluid mixture into a solid. In some instances, the devices and methods discussed herein can be used to measure mechanical properties at temperatures and pressures that simulate downhole conditions.

As used herein, "tube" and "tubular" encompass hollow members (e.g., hollow members made of metal, glass, rubber, or other material) with open ends. Such hollow members can be, but are not necessarily, cylindrical in shape.

As used herein, "piston" encompasses driving mechanisms including, for example, hydraulic pistons, power screws, and linear actuators. Thus, the piston does not necessarily seal against the pressure vessels described below.

Referring to FIGS. 1A-1F, a cement testing apparatus 100 includes a double cell test module 110 disposed inside a pressure vessel 112. The pressure vessel 112 includes side walls 118 extending between a lower end cap 120 and an upper end cap 122. The illustrated testing apparatus 100 is substantially cylindrical in shape. However, in some embodiments, the testing apparatus 100 can have other shapes (e.g., can be substantially rectangular in shape). In this description, terms of relative orientation such as upper, lower, above, and below are used relative to the orientation of embodiments shown in the figures being discussed. Although such terms do not require that the illustrated devices be oriented as shown in the figures, the cement testing apparatus 100 will typically be oriented as shown in FIG. 1A during use.

The double cell test module 110 includes a compression cell 114 and a tension cell 116. The compression cell 114 includes a first tubular flexible member 124 that extends from the lower end cap 120 of the pressure vessel 112 to the tension cell 116 of the test module. The lower end of the first tubular flexible member 124 is press-fit into a groove formed in an inner face of lower end cap 120 of the pressure vessel 112. The upper end of the first tubular flexible member 124 is press-fit into a groove formed in the lower face of the tension cell 116. Other positioning mechanisms of the first tubular flexible member can, for example, comprise an o-ring pressure seal. The first tubular flexible member 124 provides the walls of the compression cell 114 defining a compression cell sample volume 126 as a first interior volume of the sample cell. In the illustrated embodiment, side walls 118 are provided by an open ended hollow cylinder. An annular space 128 extends around the first tubular flexible member 124, between the first tubular flexible member 124 and the side walls 118 of the pressure vessel 112. The annular space 128 enables compressive testing of cement in the compression cell sample volume 126 without interference due to contact between the compression cell 114 and the side walls 118 of the pressure vessel 112 and also enables application of confinement/radial stresses.

The first tubular flexible member 124 is configured to contain a cement slurry as the cement slurry cures without providing significant resistance when compressive forces are applied to the cement sample. The first tubular flexible member 124 is a cylindrical rubber sleeve. In some embodiments, the first tubular flexible member 124 has different shapes. The first tubular flexible member 124 can be molded from rubber. Alternatively, the first tubular flexible member 124 can be formed using machining or laminating techniques from materials including, for example, epoxy, resins, and polymers.

The tension cell 116 extends from the compression cell 114 to a piston 130. The tension cell 116 includes three wall members 132, 134, 136 defining a tension cell sample volume 138 as a second interior volume of the sample cell. The tension cell sample volume 138 is axially aligned with the compression cell sample volume 126. Movement of the piston 130 in a first direction applies compression to a portion of the cement sample in the compression cell sample volume 126 and movement of the piston 130 in the opposite direction applies tension to a portion of the cement sample in the tension cell sample volume 138. Each test can be performed in any order and with no influence over the adjacent sample. The piston can be machined from stainless steel. Alternatively, the piston 130 can be formed using casting, laminating, or molding techniques from materials including, for example, steel, alloys, or composite fibers with a resin structure.

The lower wall member 132 is mechanically attached to the middle wall member 134 to form a combined unit 146 which is slidably mounted on the first attachment members 148. The first attachment members 148 are slid through the combined unit 146 and are mechanically attached to the lower end cap 120. The first attachment members 148 also function to limit movement of the combined unit 146 towards the piston 130. For example, in this embodiment, the first attachment members can be elongated rods fixed in position relative to an end wall of the sample container opposite the piston or the limiting mechanism could be, for example, an offset wall employed to limit the combined unit. The elongated rods extending through bores 150 defined in the combined unit 146. The elongated rods have flanged heads 152 and threaded tips 154. The threaded tips 154 of the elongated rods are screwed into engagement with the lower end cap 120 of the pressure vessel 112. The bores 150 are sized such that the combined unit 146 can slide along the attachment members 148. The flanged heads 152 of the elongated rods can limit movement of the combined unit 146 towards the piston. Some embodiments use other methods of attachment including, for example, pressfit engagement, threaded engagement, or J-lock attachment mechanisms.

The upper wall member 136 defines recesses 156 which receive the flanged heads 152 of the elongated rods. The recesses 156 are sized such that downward movement of the piston 130 and upper wall member 136 can push the combined unit 146 of the lower wall member 132 and the middle wall member 134 downward along the elongated rods to compress a cement sample in the compression cell sample volume 126. The piston 130 is mechanically attached to the upper wall member 136. The upper wall member 136 abuts the middle wall member 134 but is not fixedly attached to the middle wall member 134.

Figure 1C:
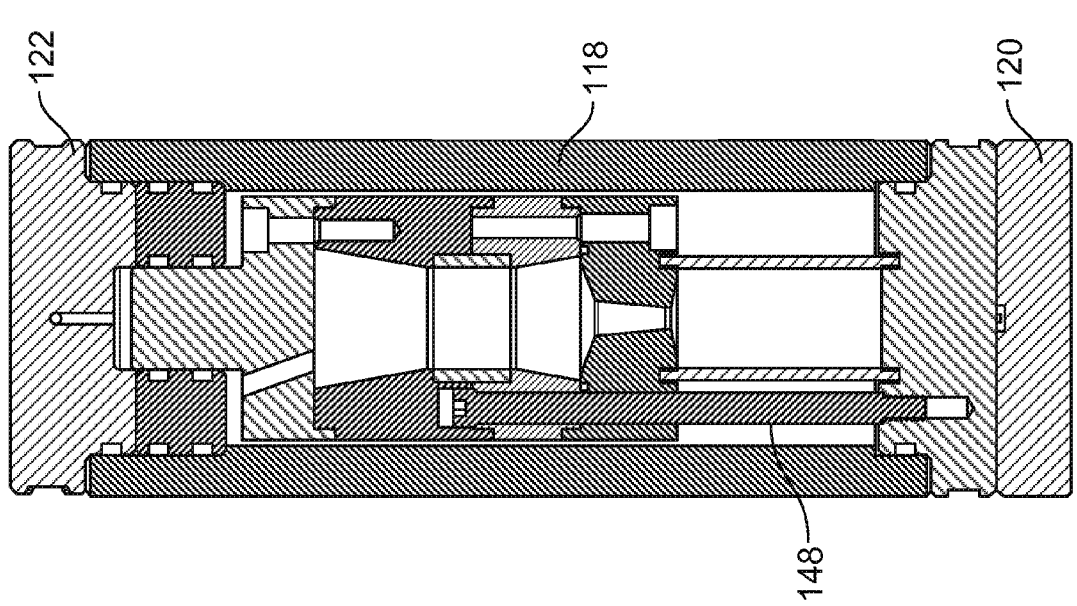
Figures 1D, 1E:
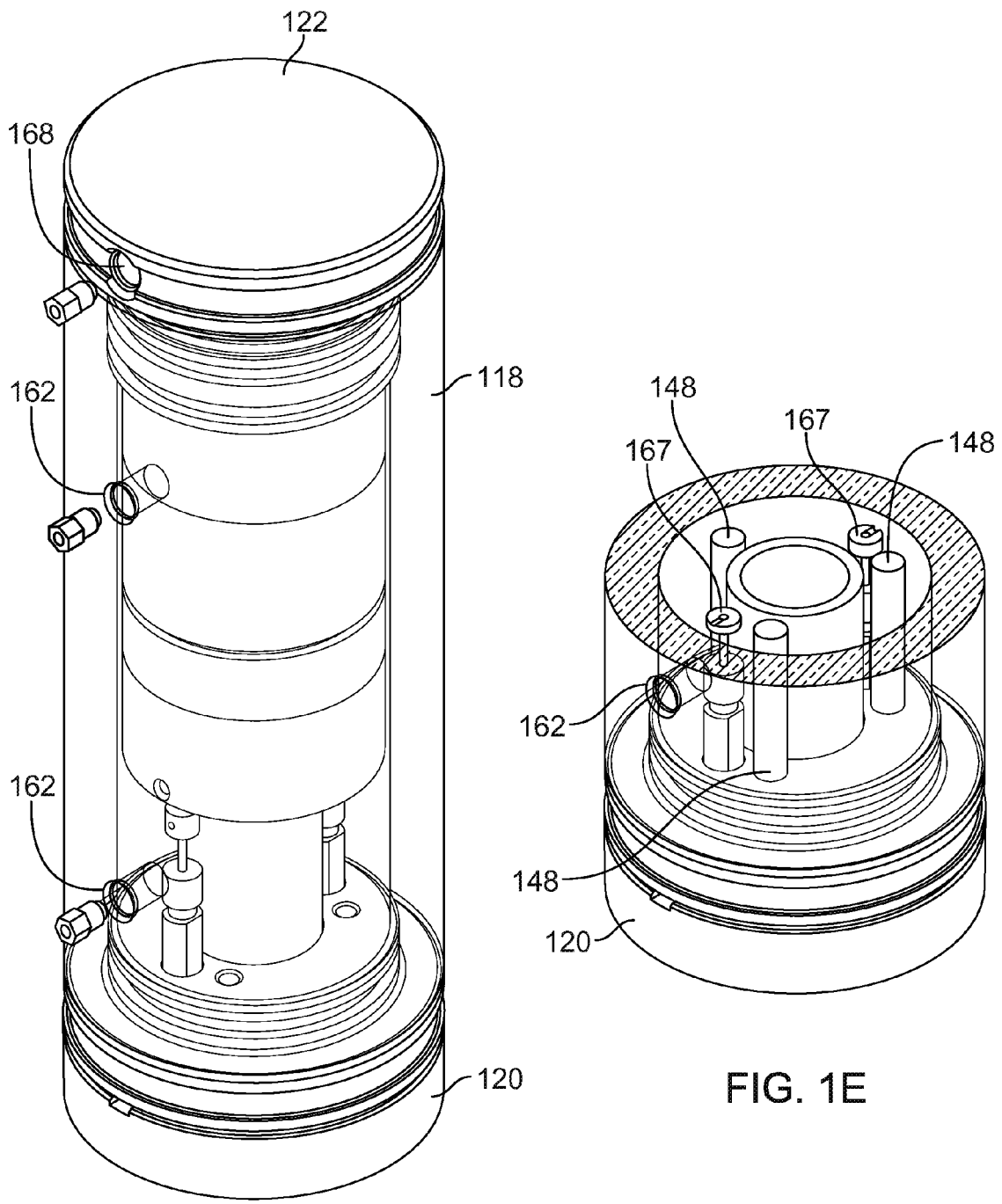
FIG. 1D is a partially transparent perspective view of the cement testing apparatus of FIGS. 1A-1C.
FIG. 1E is a truncated partially transparent perspective view of the cement testing apparatus of FIGS. 1A-1D.

The illustrated embodiment includes three attachment members 148 disposed 120° apart around the circumference of the cylindrical tension cell 116 (see FIG. 1E). Similarly, the lower wall member 132 is attached to the middle wall member 134 by three screws 140 disposed 120° apart around the circumference of the cylindrical lower and middle wall members 132, 134. Only one of the three attachment members 148 and one of the three screws 140 are shown in FIG. 1A as the other attachment members 148 and screws 140 are not in the plane shown in FIG. 1A. Some testing apparatus embodiments include fewer or more attachment members 148 and/or screws 140. Some testing apparatus embodiments include other attachment members such as, for example, mechanically locking mechanisms, and clamps. Sealing components can be disposed in the in the groove and can limit leakage between the second interior volume 138 and annular space 128 through the tension wall member 132 and 134.

The upper wall member 136 and the middle wall member 134 together define a recess 142 sized to receive a second sleeve 144. The second sleeve 144 is disposed extending across the interface between the middle wall member 134 and the upper wall member 136. The second sleeve 144 can be configured and installed such that the second sleeve 144 does not interfere with separation of the middle wall member 134 and the upper wall member 136 during tension testing.

The middle wall member 134 and the upper wall member 136 are tapered toward each other such that the tension cell sample volume 138 has a dog-bone shape with a narrow middle portion at the interface between the middle wall member 134 and the upper wall member 136. In other words, the transverse cross-section CS1 of the tension cell sample volume 138 taken at the intersection between the middle wall member 134 in the upper wall member 136 is smaller than at least one transverse cross-section CS2 of the tension cell sample volume 138 taken at a location within the middle wall member 134 and at least one transverse cross-section CS3 of the tension cell sample volume 138 taken at a location within the upper wall member 136. The cement sample in the tension cell sample volume 138 will typically fail in tension at this narrow middle portion of the tension cell sample volume 138 when the upper wall member 136 is pulled away from the middle wall member 134 as discussed in more detail below.

In this embodiment, the second sleeve 144 is a cylindrical rubber sleeve. In some embodiments, the second sleeve 144 has different shapes. In some embodiments, the second sleeve 144 is made of different materials such as, for example, high temperature elastomers or resins, and epoxies.

The lower wall member 132 defines an aperture connecting the compression cell sample volume 126 and the tension cell sample volume 138. As described in more detail below, the compression cell sample volume 126 can be filled through the aperture in the lower wall member 132. The wall segments (e.g., first tubular flexible member 124, lower wall member 132, middle wall member 134, and upper wall member 136) of the full cell test module are connected to each other such that movement of the piston 130 in a first direction applies compression to a portion of the cement sample in the compression cell sample volume 126 and movement of the piston 130 in the opposite direction applies tension to a portion of the cement sample in the tension cell sample volume 138 with no effects on the adjacent sample.

As described above, the pressure vessel 112 includes side walls 118 extending from a first end cap 120 a second end cap 122. The side walls 118 include ports 162 which can be used, for example, to introduce pressurizing fluid into the pressure vessel 112. A counterbore 164 is formed in the end of the cylinder providing the side walls 118 that receive the isolation ring 166, which is inserted into the cylinder against the end of the counterbore 164. The isolation ring 166 can isolate the fluid being used to apply the axial stress from the fluid being used to apply the confining stress.

Some configurations do not include the isolation ring or the associated counterbore. The second end cap 122 includes a port 168 connected to a channel 170 extending through the second end cap 122. Hydraulic fluid (e.g., oil based fluid, water, etc.) used to control movement of the piston 130 is applied to the piston 130 through the port 168 and the channel 170. Some embodiments of the devices use other driving mechanisms including, for example, hydraulic pistons, power screws, and linear actuators.

A central protrusion 158 of the first end cap 120 is sized to fit snugly within the side walls 118. Similarly, a central protrusion of the second end cap 122 is sized to fit snugly within the side walls 118. The central protrusion of the second end cap 122 is larger than the central protrusion of the first end cap 120. However in the configurations with no isolation ring 166, this protrusion is no longer needed.

During use, the temperature of fluid in the pressure vessel 112 can range from below ambient condition temperatures to the high temperatures associated with downhole conditions (e.g., up to 1000 degrees Fahrenheit). The pressure of the fluid in the pressure vessel can range from atmospheric pressure to the high pressures associated with downhole conditions (e.g., up to 60,000 psi). The components of the pressure vessel 112 can be made from materials which are strong (e.g., able to maintain structural stability when subjected to high pressures), are durable (e.g., resistant to corrosion by the anticipated pressurizing fluids in the anticipated temperature and pressure ranges), and can be formed with the precision necessary to maintain substantially pressure-tight engagement between the components under testing conditions. For example, the end caps 120, 122 and sidewall member 118 as well as the bottom, middle and top wall members can be machined from stainless steel. Alternatively, the end caps 120, 122 and sidewall member 118 can be formed using casting, laminating, or molding techniques from materials including, for example, steel, alloys, or composite fibers with a resin structure.

Seals can limit (e.g., substantially prevent) leakage between the first end cap 120 and the side walls 118, between the second end cap 122 and the side walls 118, between the isolation ring 166 and the side walls 118, and between the isolation ring 166 and the piston 130 (if the isolation ring is employed), and also in between the bottom and the middle wall members, 132 and 134, respectively. In the illustrated embodiment, O-rings 160 disposed in recesses extending around the central protrusions 158 and around the isolation ring 166 provide the seals. In some embodiments, pressure vessels can use other sealing mechanisms including, for example, matching threads, gaskets, or metal-to-metal seals.

Testing apparatuses can include sensors to measure parameters used to calculate properties of samples being tested. For example, testing apparatus 100 may include linear variable displacement transducers 167 (LVDTs) in suitable positions around the compression cell sample volume 126 and or the tension sample volume 138. The average reading of the LVDTs can be used to characterize the length change of the sample during testing. In addition, LVDTs can be used to measure tangential changes in deformation of the sample. Other sensors, such as extensometers, electrical strain gauges, lasers, DVRTs, or fiber optic strain gauges, can be used in addition to or in place of the LVDTs to measure relevant parameters. For example, four strain gauges (two vertical and two tangential) could be attached to interior surfaces of first tubular flexible member 124 to provide material data that would be difficult to obtain otherwise. Alternatively, strain gauges could be attached to exterior surfaces of first tubular flexible member 124. Similarly, the amount of fluid (e.g., water) pumped into the pressure vessel 112 as the cement cures can provide a measure of cement shrinkage. Pressure and temperature sensors can be included to measure pressures and temperatures present during testing. Pressure, temperature, and strain sensors can be used as feedback to control the test process. For example, pressure sensors can control the pump to pressure up or down dependent upon a controlled set point. Likewise, the piston loading the test specimen can be actuated in a direction depending on the deflection or strain measurements experienced by the sample.

As shown the FIGS. 1C-1E, the exemplary test apparatus 100 includes two MicroStrain S-DVRTs 167 (Differential Variable Reluctance Transducers) with 6-mm of linear stroke, 0.6-μm of resolution, and with an operative temperature range up to 347° F. Furthermore, a signal conditioner and a data acquisition system are also employed to measure displacement of the portion of the cement sample in the compression cell 114. The exemplary test apparatus 100 includes high accurate Honeywell pressure gages of 10,000 psi capacity, an accuracy of 0.5% of full scale and a 0-5 V amplifier. Both pressure and temperature controllers are used in such way that (a), downhole conditions are simulated during cement transferring, curing and testing; and (b) these conditions are accurately maintained or shift according to the downhole conditions. For instance, cement slurry and testing apparatus can be preheated during mixing. External or internal heating elements may be employed to keep the desired temperature on the cement slurry; or the testing apparatus could be placed in an oven for heating purposes. Examples of external heating elements include heating coils or stainless steel heating bands and, internal heating coils include, for example, internal electrical resistances inside the hydraulic fluid. There are applications where the temperature below ambient conditions are present in the wellbore, Cooling coils can be employed to take the cement specimen to the desire conditions and allow for its controlled curing. A double purpose heating/cooling system may be employed, where a hot fluid is employed when temperatures higher that ambient conditions are required; or a refrigerant is employed when temperature below ambient conditions are required. The testing apparatus can be heated in a sequence that simulates the temperature conditions that a cement system would encountered from mixing, placement, and curing during the cementing a wellbore casing string. In addition, the test apparatus can simulate other well operation events that the cement system may be exposed to including, for example, pressure testing, steam injection, fracturing, and hydrocarbon production. As anticipated, tests performed using a prototype testing apparatus have confirmed that changes in the curing temperature and pressure change the properties or mechanical response of the cement sample.

The testing apparatus 100 can be used to perform a variety of tests on cement samples including, for example, tests for uniaxial compressive strength, triaxial compressive strength, uniaxial tensile strength, and hydrostatic strength. As discussed above, the cement testing apparatus 100 can be used to perform both compressive and tensile strength tests on a single cement sample.

Compressive tests are performed by applying an axial compressive force to the sample. In contrast, direct tensile strength tests are performed by applying an axial pulling force on the sample. In either compressive or tensile strength tests, the force is, in some cases, gradually increased until the cement sample has failed, or seen the maximum amount of force available has been applied. Besides studying the mechanical response of cement systems exposed to a single loading condition, it is also valuable to determine the response of cement under multiple loading events or fatigue considering that it is well known that repetitive loading cycles will decrease the capability of the system of withstanding failure. This will allow for simulation of the load history (well operations) that the cement system will encounter during the life of the wellbore. Measurements are made of the force, axial deformation ($\Delta L$), and diametric deformation ($\Delta D$). From this information the engineering parameters normal stress ($\sigma$), axial strain ($\epsilon a$), lateral strain ($\epsilon l$), Young's Modulus (YM) and Poisson's Ratio (PR) as well as the compressive strength (CS), and yield point, can be determined.

Normal stress is defined as a force applied perpendicular to a unit of area. Axial strain is defined as the amount of dimensional change ($\Delta L$) relative to the original length ($L0$) in the direction of primary stress. Lateral strain is defined as the amount of dimensional change (ΔD) relative to the original Diameter (D0) in a direction perpendicular to the primary stress. Likewise, when cement samples are confined at pressure greater that ambient conditions, the net stress applied to the sample is the difference between the normal stress and the confining stress. Similarly, the net strength will be the difference between the ultimate net stress and the confining stress.

Figure 5:
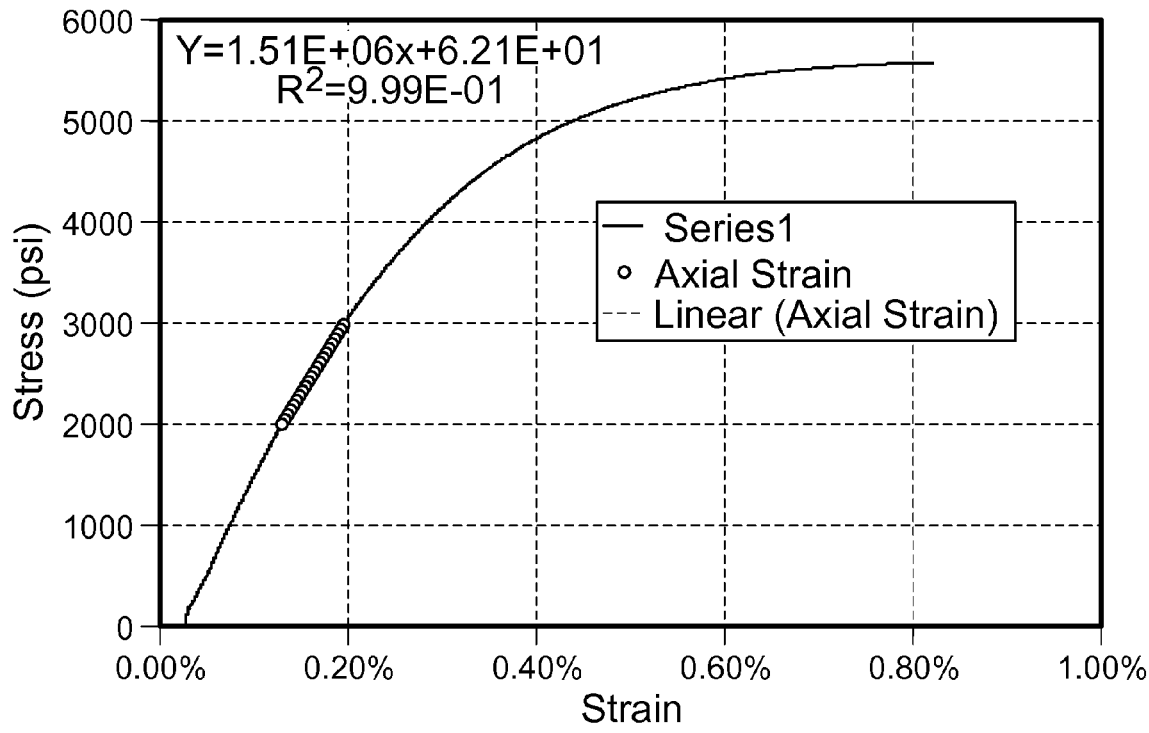
FIG. 5 shows the stress strain relationship during compression testing (compressive Young's Modulus).

The results of cement compressive tests can be presented as stress versus strain as shown in FIG. 5. In rock mechanics, compressional stress is typically defined as positive; thus, a reduction in dimension is presented as a positive strain. For the example stress-strain curve, the positive strain (ε) portion of the x-axis is equivalent to the axial strain (εa). The curve associated with positive strain is measured and mathematically derived from the axial deformation and pressure sensors in an individual testing apparatus. When cement is deformed axially in compression, it has the tendency to expand in the lateral direction. This results in a strain value that is negative. The curve associated with the negative strain values, or lateral strain (εl) is derived from the diametric deformation and pressure sensors in an individual testing apparatus.

Young's Modulus (YM) is a measure of the stiffness of an isotropic elastic material and is defined as the ratio of the axial stress over the axial strain in the range of stress in which the material has a tendency to deform linearly under stress. In moderate stress levels, cement typically deforms linearly and therefore its modulus is often reported. The Young's Modulus of a cement sample is determined experimentally by taking the slope of a linear regression on the stress-strain plot over a known stress range (see, e.g., the darkened portion of the positive strain curve in FIG. 5). In other methods, the Young's Modulus can be derived on different portions of the stress-strain curve or from zero to a point along the stress-strain curve.

Poisson's Ratio, which characterizes the lateral deformation as a function of axial deformation is the ratio, when a sample object is stretched, of the contraction or transverse strain (perpendicular to the applied load), to the extension or axial strain (in the direction of the applied load). The Poisson's Ratio of a cement sample is determined experimentally by calculating the ratio of lateral strain change to axial strain change experienced over the same stress range.

The unconfined compressive strength is the maximum stress that cement can endure when the confining pressure (e.g., the pressure in the annular space 128 of the pressure vessel 112 outside of the test module 110) is zero. It is determined experimentally by destructively testing the cement. The maximum stress recorded at failure is the unconfined compressive strength.

Compressive testing can also be performed with stresses applied in more than one direction. For example, a confining pressure can be used to apply fluid pressure on the lateral side surfaces of a sleeved test specimen in compression cell sample volume 126 (see FIG. 1A). This results in a stress ($\sigma 2$) along the curved surface equal to the fluid pressure. The primary stress ($\sigma 1$) can still be applied mechanically through the hydraulic system. The unconfined compression test is a simplified version of the triaxial test with the confining stress ($\sigma 2$) left equal to zero. The engineering parameters, previously discussed, can also be determined for a test result where the stress-strain relationship is recorded. If multiple sets of triaxial compressive tests are performed, friction angle and cohesion can also be determined by recording the maximum axial stress ($\sigma 1$) versus the confining stress ($\sigma 2$).

Other configuration of the testing apparatus can allow the pore pressure to be controlled separately from the confining pressure. Likewise, pore pressure controlled can be set equal to the curing pressure or the confining pressure or set at random value. This will allow the user to study the effect of different pore and confining pressure on the sample mechanical response.

Endurance limit or the capacity of the cement system to withstand fatigue can also be determined. Knowing the endurance limit as a "the value of stress at which failure occurs after N number of cycles" according to ASTM. This property is key for oil well cementing applications considering that various well operation processes take place during the life of the well and it turns out important to account for these stages during the design of the cement system ensuring zonal isolation during the life of the well.

The maximum "pulling" stress that a cement sample can withstand is defined as the tensile strength (TS). The tensile strength of a sample can be tested indirectly or directly. Direct testing (e.g., by actually pulling on the sample until it breaks) can provide different, possibly more accurate results than indirect testing. Direct testing typically requires removing the sample from the pressure vessel in which it has been cured. The testing apparatus 100 enables direct testing of a cement sample in the pressure vessel in which it has been cured. In the same manner that compressive testing, the net tensile strength will be the absolute difference between the minimum normal stress and the confining stress.

The results of tensile strength testing can be plotted on stress-strain curves and analyzed in similar fashion to that discussed above for analyzing the results of compressive testing.

A user preparing and filling the testing apparatus 100 for testing of a cement sample begins by attaching the first rubber sleeve 124 to the bottom end cap 120 of the compression cell 114 and to the lower wall member 132 of the tension cell 116. Typically, the bottom end cap 120 of the compression cell 114 will be resting on a flat working surface such as a table. The middle wall member 134 of the tension cell 116 is placed on top of the lower wall member 132 and attached to the lower wall member 132 using screws 140. The long screws (used as the attachment members 148) are inserted through the bores 150 defined extending through lower wall member 132 and the middle wall member 134. The long screws (attachment members 148) are then threaded into the bores defined in the lower end cap 120. The second sleeve 144 is then inserted into the portion of recess 142 defined by the middle wall member 134. The upper wall member 136 is then placed on top of the middle wall member 134 with the heads 152 of the screws 140 received in the recesses 156 of the upper wall member 136 and the second sleeve 144 received in the portion of the recess 142 defined by the upper wall member 136. The cylinder providing sidewalls 118 of the pressure vessel 112 is then lowered around the compression cell 114 and the tension cell 116 and attached to the lower end cap 120.

A cement slurry to be tested is dispensed into the testing apparatus 100 through the open upper end of the upper wall member 136 to fill the compression cell sample volume 126 and the tension cell sample volume 138. The piston 130 is placed on top of the upper wall member 136 and attached to the upper wall member 136 using, for example, screws 140. The isolation ring, if implemented, 166 is inserted into the counterbore 164 of the cylinder providing the side walls 118 of the pressure vessel 112. The isolation ring 166 extends between the piston 130 and the side walls 118. The upper end cap 122 is placed onto and attached to the side walls 118.

The sidewall member 118 is attached to the end caps 120, 122 by pressfit engagement between the sidewall member 118 and the end caps 120, 122. This configuration provides for easy assembly and disassembly of the pressure vessel 112. However, this configuration can require an external locking mechanism (not shown) to hold the pressure vessel 112 together as a pressurizing fluid is supplied to the interior volume of the pressure vessel. In some embodiments, the end caps 120, 122 and the sidewall member 118 have matching threads on the exterior surfaces of the end caps 120, 122 and the corresponding to interior surfaces of the sidewall member 118. In these embodiments, the end caps 120, 122 and the sidewall member 118 can be screwed together. Alternatively, the end caps 120, 122 and the sidewall member 118 can also be attached using J-lock attachment mechanisms.

The cement slurry can be cured or partially cured at controlled temperatures and pressures to simulate, for example, downhole conditions before testing. A temperature stable pressurizing fluid such as, for example, water is pumped into the annular space 128 between the test module 110 and the side walls 118 of the pressure vessel 112. The pressure applied to sides of the cement sample can be controlled using the pressurizing fluid. The cement slurry is allowed to cure for a specified time with an equal pressure applied to the top of the piston 130 and into the annular space 128 between the test module 110 and the side walls 118 of the pressure vessel 112. Temperature can be controlled to simulate downhole conditions during testing or at other times. For example, in testing cement, the testing apparatus 100 and cement slurry can be preheated during mixing. The desired temperature can be maintained as the sample cement composition cures using external heating elements (e.g., heater coils or stainless steel heater bands) or placing the testing apparatus 100 in an oven; cooling coils can also be employed if temperatures below ambient conditions are desired. Likewise the testing apparatus could also be heated in a profile that simulates the temperature a cement system would experience from mixing, placement, and curing during cementing a wellbore casing string. After the cement slurry has cured the desired degree, compression and tension testing are performed by regulating the pressure applied to the piston 130.

The cement testing apparatus 100 can also be configured such that a slurry of a cement sample can be mixed at pressure and temperature conditions that are different than ambient pressure conditions and then be transferred to the sample container for curing without exposure to ambient pressure conditions.

Compression testing is performed by increasing the pressure applied to the piston 130. Increasing the pressure applied to the piston 130 biases the piston 130 towards the cement sample and biases the entire tension cell 116 to towards the compression cell 114 along the attachment members 148. The recesses 156 in the upper wall member 136 are sized to allow the flanged heads 152 of the attachment members 148 to move farther into the upper wall member 136 as the tension cell 116 moves towards the compression cell 114 (e.g., when the portion of the cement sample in the compression cell sample volume 126 fails in compression). The pressure applied to the piston 130 is increased until the portion of the cement sample in the compression cell sample volume 126 fails in compression. Once failure is reached, the flanged heads 152 will act as a limiting/stopping mechanism of the tension cell 116.

Tension testing is performed by decreasing the pressure applied to the piston 130. As described above, the upper wall member 136 is not mechanically attached to the middle wall member 134. Decreasing the pressure applied to the piston 130 biases the piston 130 away from the cement sample. As the attachment members 148 limit movement of the middle wall member 134 in the lower wall member 132 away from the bottom end cap 120 of the pressure vessel 112, decreasing the pressure applied to the piston 130 also biases the upper wall member 136 away from the middle wall member 134 and the lower wall member 132. The pressure applied to the piston 130 is decreased until, in some cases, the portion of the cement sample in the tension cell sample volume 138 fails in tension; in other cases, stresses are applied up to certain levels of the ultimate stress of the sample for instance to study the sample reaction to cyclic loading events. Both the compression and tension testing can be performed in any order without affecting the integrity of the adjacent portion of the sample.

Figure 2:
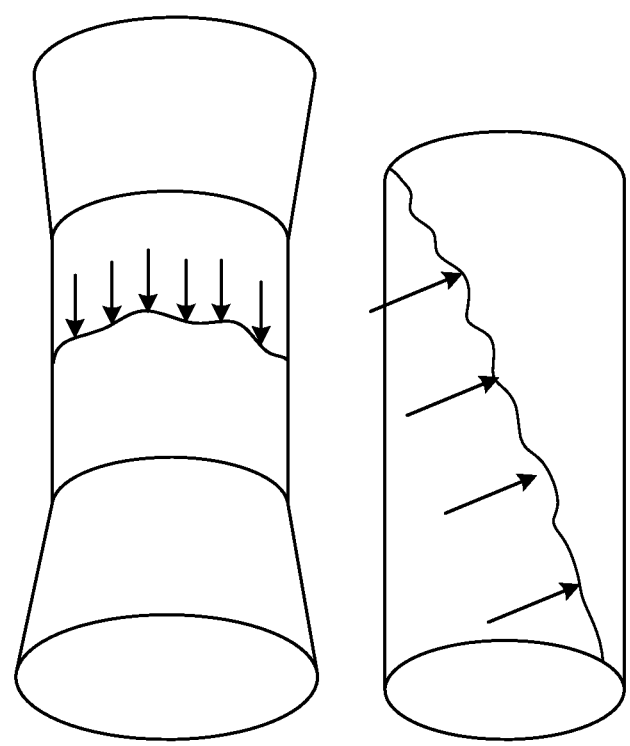
FIG. 2 shows the tension (left) and compression (right) portions of the sample after the test were performed with arrows indicate where the failure took place in each portion of the sample.

In verification testing, a prototype of a cement testing apparatus 100 as described above with reference to FIGS. 1A-1F was used to test the properties of a cement slurry under both compression and tension. After the testing apparatus 100 was assembled as described above, the test module 110 was filled with a 16.4 pound/gallon cement slurry with premium class H cement and water to cement ratio of 0.38 mixed at ambient conditions. The test module 110 and pressure vessel 112 were sealed and a confining pressure of 2000 psi was applied as the cement slurry cured for 48 hours at ambient conditions. After curing for 48 hours, the cement sample was tested under 2000 psi confining pressure and at ambient temperatures in compression until failure and then in tension until failure. FIG. 2 shows the tension (left) and compression (right) portions of the sample after the test were performed with arrows indicate where the failure took place in each portion of the sample. The location of the resulting cracks confirmed that the cell is calculating the tensile and compressive strength.

Figure 3:
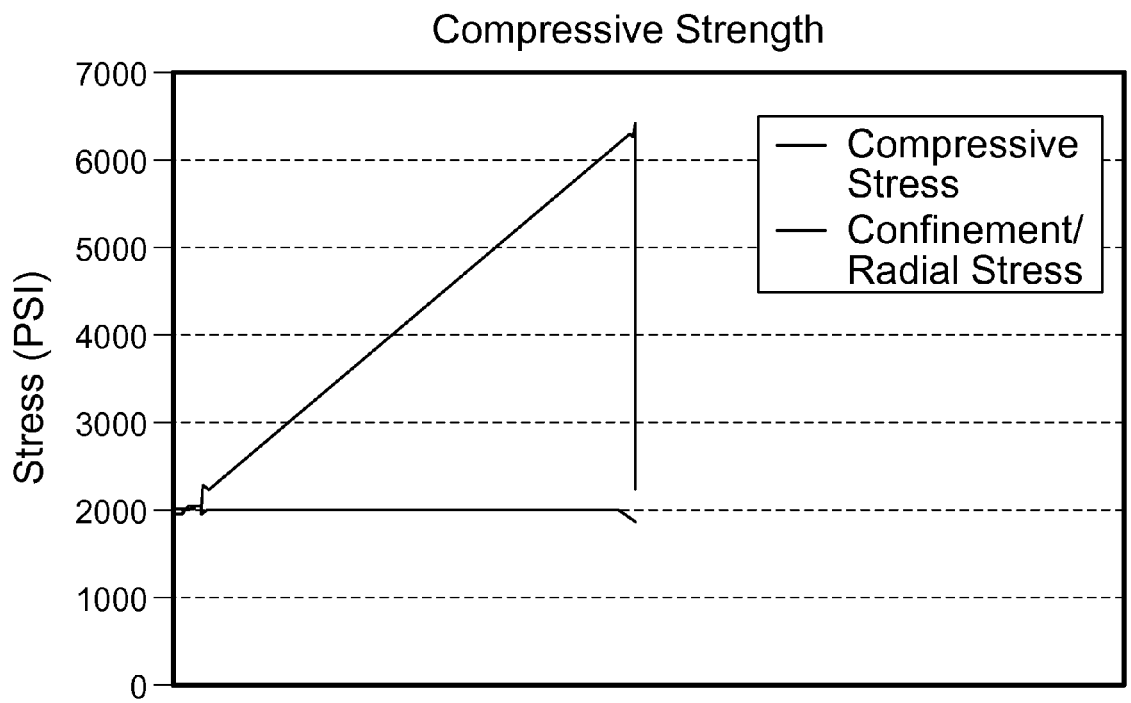
FIG. 3 shows results of a compression test of a sample cured at 2000 psi.

FIG. 3 plots the confining radial stress ($\rho 2$) (held steady at ~2,000 psi) and the axial compressive stress as a function of time. The portion of the cement sample in the compression cell 114 failed when the axial compressive stress ($\sigma 1$) being applied was increased to ~6,394 psi indicating that the net strength ($\sigma 3 = \sigma 1 - \sigma 2$) under compression of this slurry under these conditions is ~4,394 psi. This generally matched expectations considering the sample was only cured during 48 hours.

Figure 4:
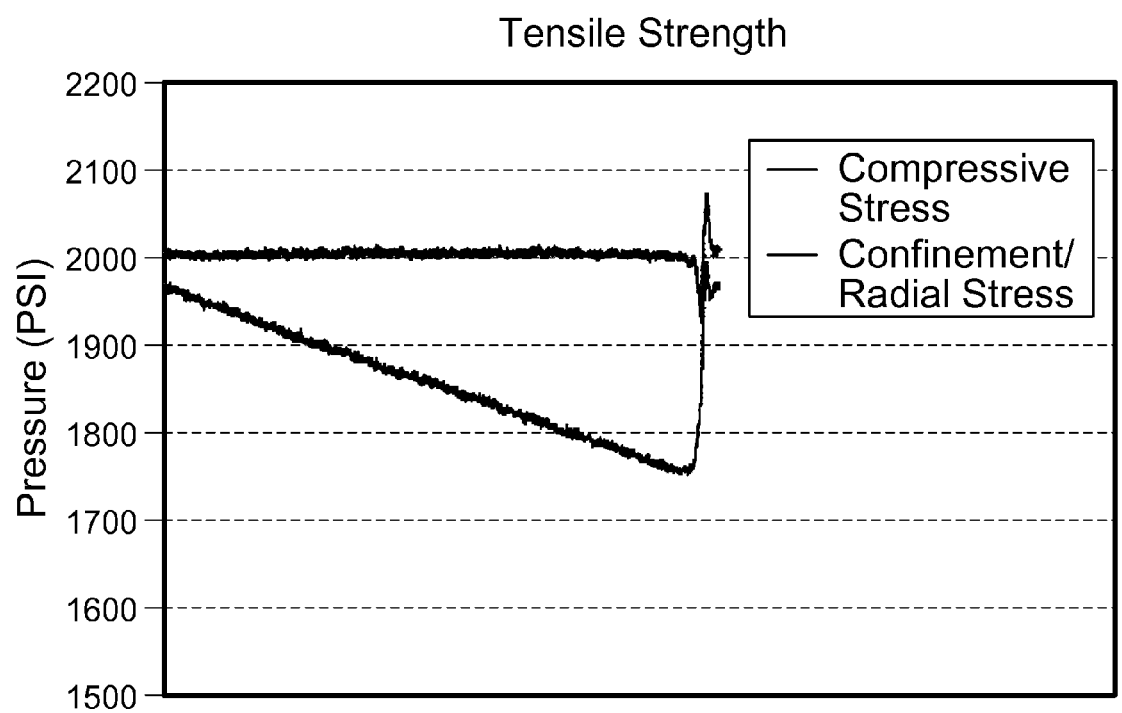
FIG. 4 shows results of a tension test of a sample cured at 2000 psi.

After the compression test was performed, the axial compressive stress was reduced gradually in order to generate failure by tension on the tension part of the specimen. FIG. 4 plots the confining radial stress (held steady at ~2,000 psi) and the axial compressive stress as a function of time. The portion of the cement sample in the tension cell 116 failed when the axial stress being applied was decreased to ~1,777 psi indicating that the net strength under tension of this slurry under these conditions was ~233 psi. This generally matched expectations considering the sample was only cured during 48 hours.

In further verification testing, the prototype of a cement testing apparatus 100 was used to test the properties of another cement slurry under both compression and tension. For comparison purposes, the cement slurry was also tested using 550,000 lb MTS load frame with radial and axial extensometers. This equipment has capabilities of running confined and unconfined tests as wells as Brazilian tensile testing (indirect tensile test) and is the current most accurate test system employed to determine mechanical properties such as compressive strength, Young's modulus, Poisson's ratio, Brazilian tensile strength, cohesion, friction angle, etc. However, large numbers of sub-equipments are required in order to determine the properties mentioned above as each test may requires different components. After the testing apparatus 100 was assembled as described above, the test module 110 was filled with a 16.4 pounds/gallon cement slurry, with premium class H cement and a water to cement ratio of 0.38, mixed at ambient conditions. The test module 110 and pressure vessel 112 were sealed and a confining pressure of 3000 psi was applied as the cement slurry cured for 5 days at ambient temperature. During the curing process, the cement sample may be exposed to constant pressure during a specified period of time, however, this pressure may vary according to the conditions downhole. After curing for 5 days under constant pressure, the cement sample was depressurized at a constant rate down to ambient conditions. Then the sample was tested at ambient conditions in compression until failure and then in tension until failure. It should be noted that along the curing process in the testing apparatus, additional samples were cured in other sample molds for testing performed with MTS for comparison. Although the MTS only has capabilities of testing samples at ambient conditions and has no curing capabilities, tests were performed in both the testing apparatus described herein and the MTS in order to use the MTS results as a standard for comparison due to the accuracy of the MTS system.

Figure 6:
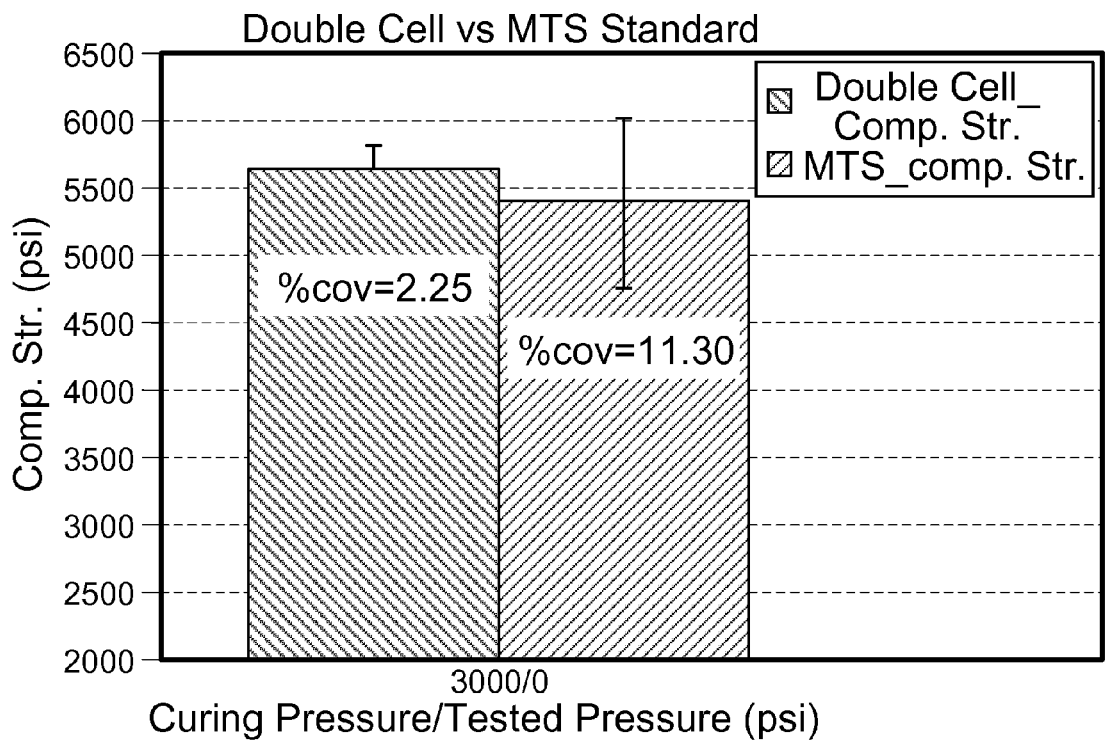
FIG. 6 and FIG. 7, respectively, compare the compressive strength and the Young's Modulus calculated based on observations from a prototype dual cell testing apparatus and a standard MTS test cell for additional verification testing.
Figure 7:
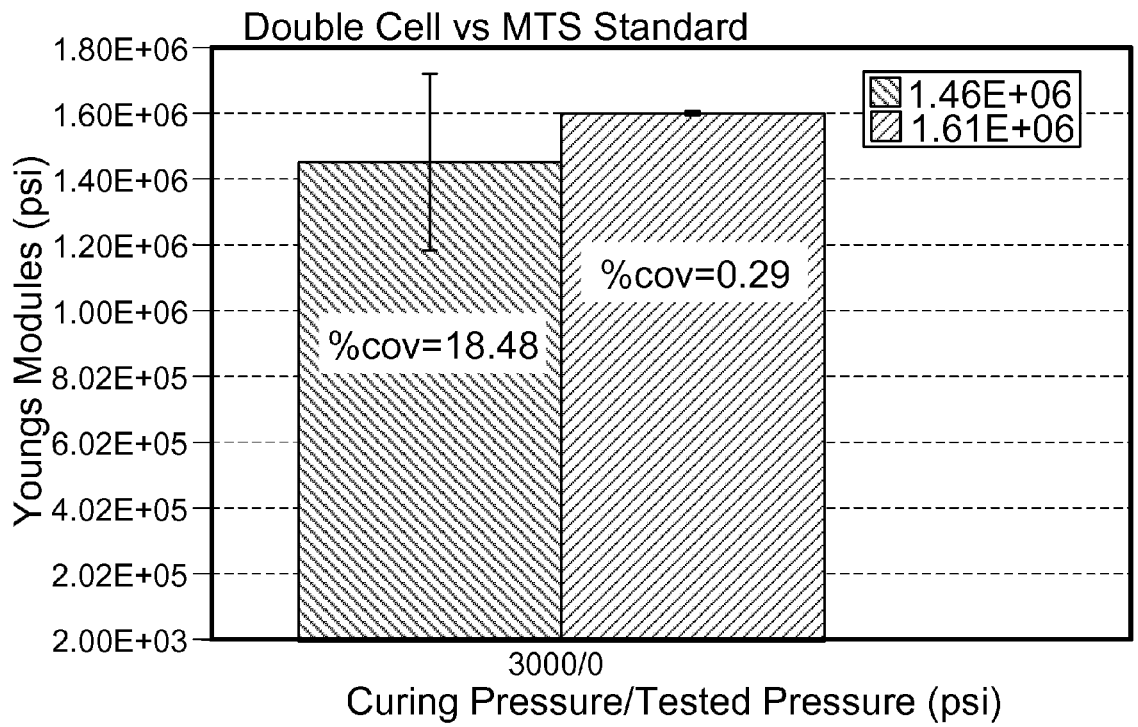

FIG. 5 shows the stress-strain relationship during compression testing. The portion of the cement sample in the compression cell 114 failed when the axial compressive stress being applied was increased to ~5,563 psi. FIG. 6 compares the compressive strength calculated based on observations from the prototype dual cell testing apparatus 100 and a standard MTS test cell. FIG. 7 compares the Young's Modulus calculated based on observations from the prototype dual cell testing apparatus 100 and a standard MTS test cell. It was observed that both the compressive strength and Young's Modulus results from the prototype dual cell testing apparatus 100 were generally consistent with those from the MTS load frame.

Figure 8:
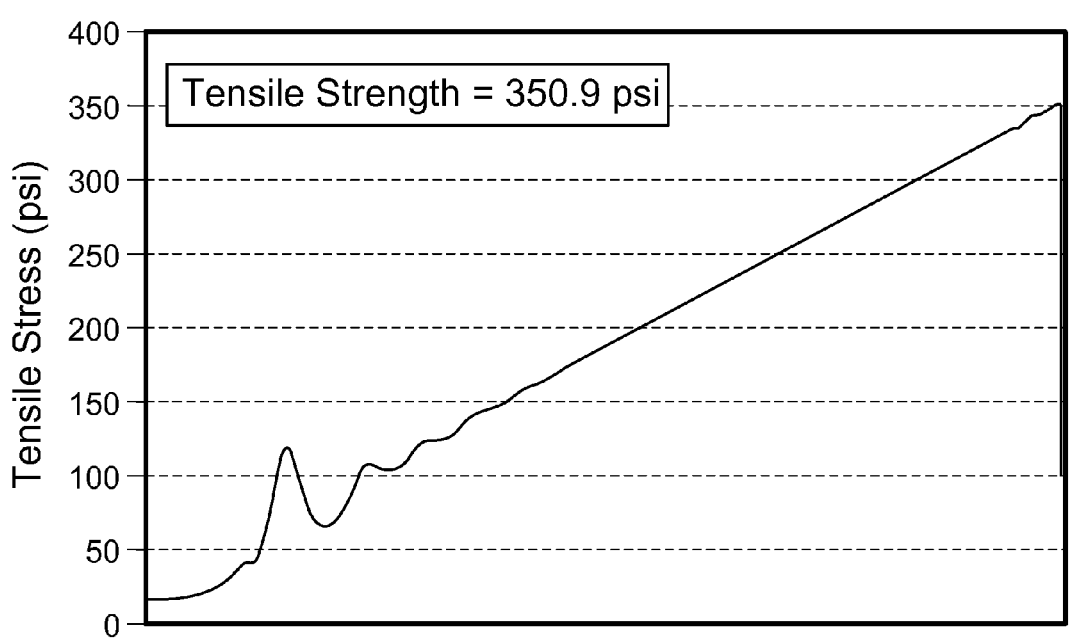
FIG. 8 shows results of a tension test of a sample cured at ambient conditions. In this case, the pressure on the side of the sample was increased in order to generate a failure in tension of the sample.

After the compression test was performed, the axial compressive stress was reduced gradually down to the initial conditions, ambient conditions in this case. In order to generate failure by tension on the tension part of the specimen, the confining stress applied to the samples is gradually increased either up to failure or to the point of interest. This is necessary considering that the confining stress applied to the sample was previously reduced to ambient pressure to generate the same conditions at which a regular MTS sample would be exposed to allow for comparison. FIG. 8 plots the axial tensile stress as a function of time. The portion of the cement sample in the tension cell 116 depressurized to ambient conditions after 5-days-curing at 3000 psi failed when the confining stress being applied was increased to ~351 psi.

The concepts discussed above can be implemented in other configurations of the testing equipment. For example, in the implementation of a cement testing apparatus 100 shown in FIGS. 1A-1E, pressure is applied only to the upper portion of the system and not to the bottom portion of the DVRTs' extension rods 167. This creates a pressure differential that is transformed into a load applied to the first tubular flexible member 124 that generates an unbalanced system.

Figure 9:
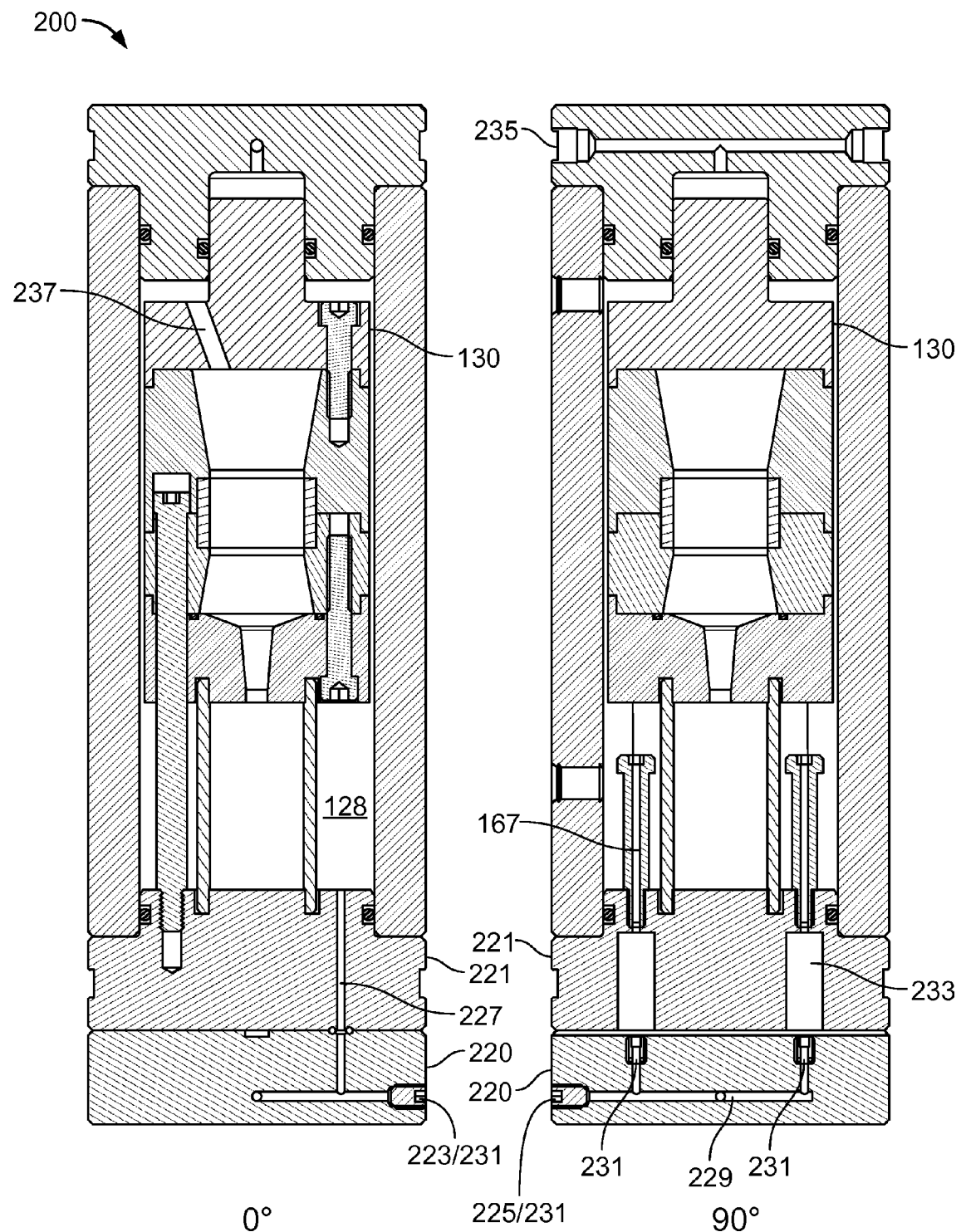
FIGS. 9-11 are cross-sections of cement testing apparatuses.

FIG. 9 includes two section views taken orthogonally to each other (one at 0 degrees and the other at 90 degrees) that illustrate a cement testing apparatus 200 that provides a pressure-balanced configuration in which the measurement devices 167 (e.g., LVDTs or DVRTs) will be exposed to the same pressure on both their top and bottom portions. The structure and functionality of the cement testing apparatus 200 is substantially the same as the structure and functionality of the cement testing apparatus 100. The main differences are additional ports and parts added to provide the pressure-balanced configuration. This system can avoid initial loadings applied to the rubber sleeve during curing due to having unbalanced system.

The cement testing apparatus 100 includes a one-piece lower end cap 120. In contrast, the cement testing apparatus 200 includes a two-piece lower end cap 220, 221. The outer portion 220 of the two-piece lower end cap 220, 221 has a first port 223 and a second port 225. These two interconnected ports allow for curing pressure application to the LVDTs, also facilitate machining/manufacturing. The inner portion 221 of the two-piece lower end cap 220, 221 defines cavities 233 sized and configured to receive the LVDTs 167. The two-piece lower end cap 220, 221 defines channels 227 that extend from a port 223 to the annular space 128. Channels 227 allow confining pressure to be applied to the bottom portion of LVDT core rod. The two-piece lower end cap 220, 221 also defines channels 229 that extend from a port 225 to set screws 231 at interface with cavities 233 which allows for pressure application to the bottom portion of the LVDTs. The channels 227 and the channels 229 are interconnected. These set screws 231 along with o-ring seals limit (e.g., prevent) fluid contact with the electronics of the measurement sensors. Set screws 231 are also provided to block ports 223, 225, and avoid any fluid leaks towards the outside of the cell.

The cement testing apparatus 200 does not include an isolation ring 166. Rather, the upper end cap 122' is structurally and functionally similar to a one-piece combination of the upper end cap 122 and isolation ring 166 of the cement testing apparatus 100. The modified upper end cap 122' defines a second port 235 that has been added to the upper end cap 122' to allow for air removal during use. This modified upper end cap 122' can simplify assembly and use of the cement tester. Although this cell configuration can provide easy assemble/disassembly of the pressure vessel, this configuration may need an external locking mechanism (not shown) to hold the pressure vessel while hydraulic fluid is supplied and pressurized in the interior volume.

The piston 130' defines a bore 237 extending through the piston 130'. The bore 237 allows equal confining and pore pressure to be applied to the samples being tested. This configuration does not provide independent control over these 2 variables. However, cement tester configurations including an upper piston without the bore 237 and adding a port in the lower end cap can provide for independent control of pore pressure and confining pressure.

Other configuration of the testing apparatus can allow the pore pressure to be controlled separately from the confining pressure. These configurations allow, for example, pore pressure controlled to be equal to the curing pressure or the confining pressure or set at random value. This will allow the user to study the effect of different pore and confining pressure on the sample mechanical response. This can be accomplished by independently controlling the confining pressure and the pore pressure.

Figure 10:
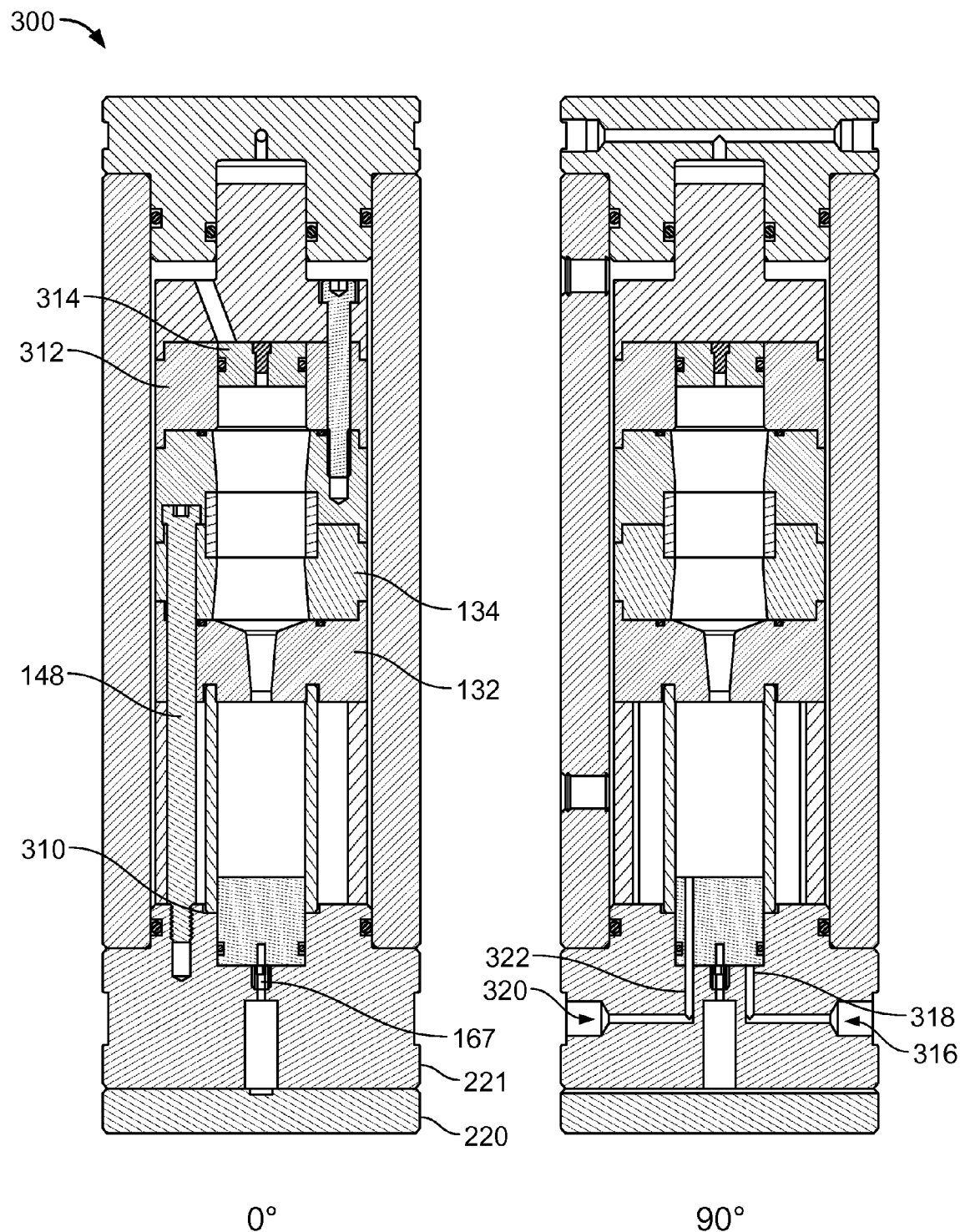

FIG. 10 includes two section views taken orthogonally to each other (one at 0 degrees and the other at 90 degrees) that illustrate a cement testing apparatus 300 incorporating a bottom piston that can provide independent control on confining pressure and pore pressure. This simpler system includes a single measuring device 167 placed axially with respect to the sample.

The cement testing apparatus 300 is substantially similar to the cement testing apparatus 200 but includes a bottom piston 310 and, optionally, a confining ring 312 and a piston 314. If equal confining and pore pressure are wanted, the confining piston 314 and the plug are not necessary. However, including the confining piston 314 and the plug can provide independent control of the confining pressure and the pore pressure.

Axial stresses are applied to the bottom piston 310 which transfers the stresses to the sample during compression testing.

In this configuration, the attachment members (e.g., screws 148) limit the movement of the lower and middle tension cell wall members 132, 134. In addition, when the bottom piston 310 applies pressure over the compression sample, the attachment members 148 hold the sample compression system in place in such a way that only the samples is deformed.

The inner portion 221 of the two-piece lower end cap 220, 221 defines a cavity 233 sized and configured to receive the sensor (e.g., LVDT 167). Because the LVDT is axially positioned with respect to the sample, only one sensor 167 is required. Moreover, the sensor 167 is axially positioned with respect to the sample with only the piston between the sensor 167 and the sample. Theoretically, this arrangement will result in more accurate measurements.

The inner portion 221 of the two-piece lower end cap 220, 221 defines a port 316 and an associated channel 318 operable to apply axial pressure on the bottom piston 310 to exert axial stresses to the compression sample. The inner portion 221 of the two-piece lower end cap 220, 221 and the bottom piston 310 define a port 320 and an associated channel 322 which, when the confining piston 314 and plug are employed to allow for control on confining pressure, can allow for independent control of pore pressure as well.

A spacer ring 324 limits the movement of the tension cell 116 towards the compression cell 114 avoiding any changes on the shape and initial geometry of the compressive sample while curing. Moreover, any pressure applied on the piston 130 would be absorbed by the spacer ring without affecting the integrity of the sample, conversely, it would help the function of the attachment members 148.

Figure 11:
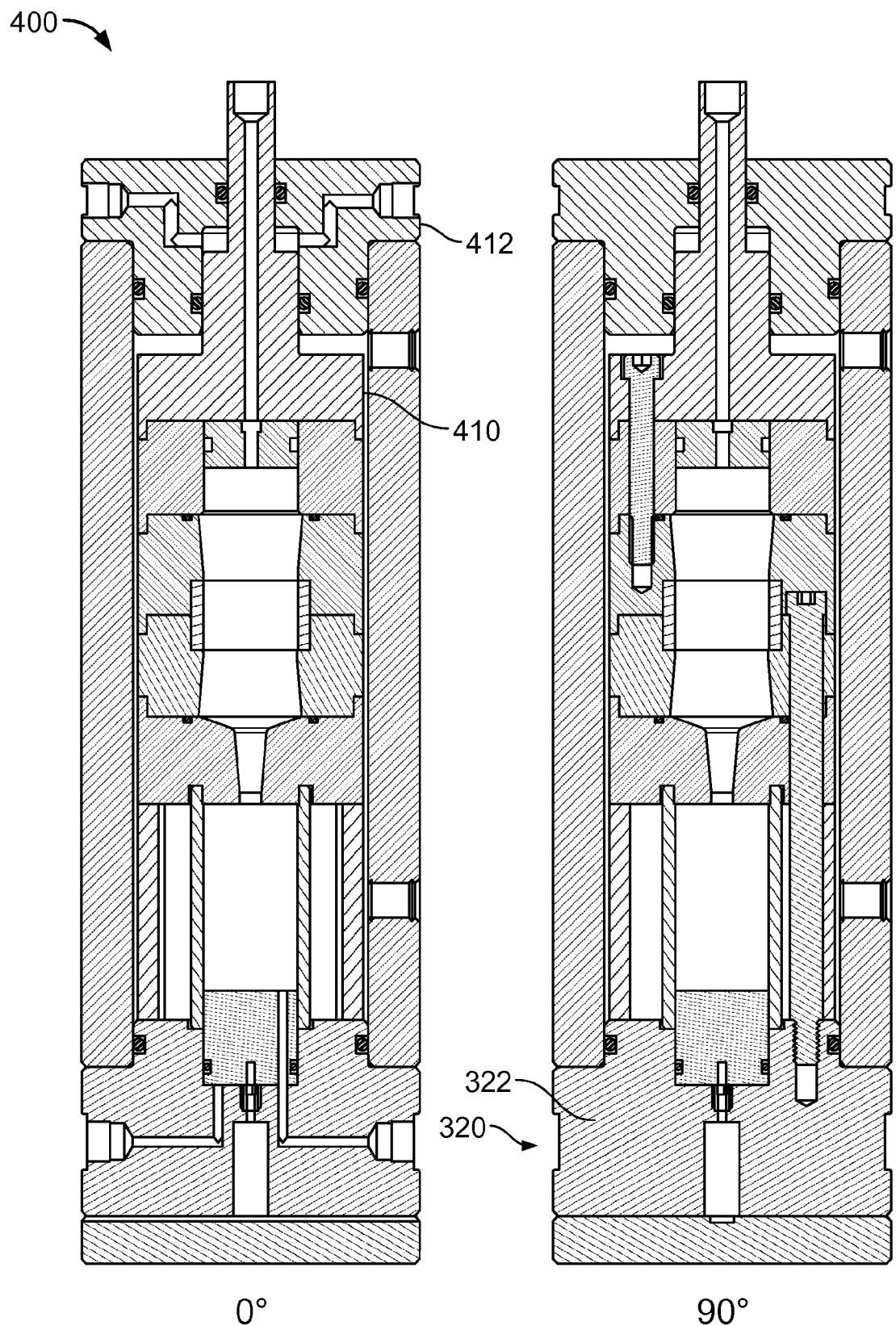

FIG. 11 includes two section views taken orthogonally to each other (one at 0 degrees and the other at 90 degrees) that illustrate a cement testing apparatus 400 configured such that a slurry of a cement sample can be mixed at pressure and temperature conditions that are different than ambient pressure conditions and then be transferred to the sample container for curing without exposure to ambient pressure conditions. The cement testing apparatus 400 is substantially similar to the cement testing apparatus 300. However, the cement testing apparatus 400 includes a modified piston 410 and upper end cap 412. The piston 410 defines a channel that can be used to controllably vent gases as interior spaces of the cement testing apparatus 400 are filled with a pressurized cement slurry through port 320 and channel 322. U.S. Pat. No. 5,869,750 and US Patent Publication Number 2011/0094295 discuss methods and equipment that can be used in preparing and testing a slurry of a cement sample without exposure to ambient pressure conditions. The entire contents of these references are incorporated herein by reference.

The methods and systems described can allow a liquid slurry to cure at controlled pressure and temperature conditions and, while curing or after cured, to be tested for volume changes, the mechanical response of the sample, and failure limits without removing curing, or cured, cement from the testing apparatus. Testing in the curing vessel can reduce the possibility that removal of the sample from the testing apparatus could impart damage to the sample that would influence subsequent results. Testing in the curing vessel can also save time and money, and reduces the limits on the ability to test curing in a small time window relative to cure associated with systems which require removal of the curing vessel for testing.

The methods and systems described can allow for testing both compression and tension in the same cell without changing components. Tubular flexible members, for both tension and compression, along the same cell allow for sample molding while keeping the same specimen's shape during the initial hydration stage. The tubular flexible members offer negligible resistance during testing. A hydraulic piston allows the application of axial stress on the cement samples while confining stress may be controlled by a pressure sources, e.g., pump. The cell is configured to cause different portions of a single sample to fail in compression and in tension without rearranging any mechanical parts, which will result in substantially reduced sample preparation and specimens test time.

The methods and systems described can provide the ability to cure and test cement at conditions that represent a cemented well casing.

A number of embodiments have been described. Nevertheless, it will be understood that various modifications may be made. For example, in some embodiments, multiple testing apparatuses 100 can be attached in parallel to pressure sources applying confining, tension, compression, and pore pressure loads. Common initial conditions can be sent across multiple testing apparatuses 100 with testing being performed, for example, at different points in the curing process. The multiple testing apparatuses 100 can also be used to replicate tests to facilitate statistical analysis of the properties of the cement being tested. Systems incorporating multiple testing apparatuses 100 are described in more detail in U.S. Patent Pub. No. 2011/0094295, which is incorporated by reference in its entirety. Accordingly, other embodiments are within the scope of the following claims.

What is claimed is:

1. A system for testing a sample, the system comprising:
at least one cement testing apparatus, each cement testing apparatus comprising:
a sample container having wall segments defining a first interior volume, a second interior volume, and an aperture extending between the first interior volume and the second interior volume;
a piston connected to the sample container;
wherein the wall segments are connected to each other such that movement of the piston in a first direction applies compression to a portion of the cement sample in the first interior volume and movement of the piston in a second direction opposite the first direction applies tension to a portion of the cement sample in the second interior volume, and
at least a portion of the wall segments are slidably mounted on a first attachment member that is coupled to an end wall of the sample container that defines, at least in part, at least one of the first or second interior volumes.

2. The system of claim 1, wherein the portion of the cement sample in the first interior volume and the portion of the cement sample in the second interior volume are axially aligned.

3. The system of claim 1, wherein at least one wall segment defining the first interior volume of the sample container is formed of a material that does not significantly increase resistance to compression of the portion of the cement sample in the first interior volume of the sample container.

4. The system of claim 3, wherein the at least one wall segment defining the first interior volume of the sample container comprises a flexible tubular member.

5. The system of claim 4, wherein the flexible tubular member is coupled between one of the wall segments and the end wall of the sample container.

6. The system of claim 1, wherein the system further comprises a pressure vessel containing the sample container.

7. The system of claim 6, wherein an interior surface of the pressure vessel partially defines the first interior volume of the sample container or the second interior volume of the sample container.

8. The system of claim 1, wherein the wall segments comprise a first tension member and a second tension member adjacent the first tension member, the second tension member disposed between the piston and first tension member such that movement of the piston in the first direction presses the second tension member towards the first tension member and movement of the piston in the second direction pulls the second tension member away from the first tension member.

9. The system of claim 8, wherein a transverse cross-section of the second interior volume taken at an intersection between the first tension member and the second tension member is smaller than at least one transverse cross-section of the second interior volume taken at a location within the first tension member and at least one transverse cross-section of the second interior volume taken at a location within the second tension member.

10. The system of claim 8, comprising a flexible tubular disposed in a recess defined by the first tension member and the second tension member.

11. The system of claim 8, wherein the first attachment member slidably engages the first tension member to limit movement of the first tension member towards the piston.

12. The system of claim 11, wherein the second tension member is attached to the piston.

13. The system of claim 11, wherein the second tension member comprises a recess into which the first engagement member is mounted, the recess defining a compressive travel distance of the second tension member on the first engagement member during movement of the piston in the first direction.

14. The system of claim 11, wherein the first attachment member is an elongated member fixed in position relative to the end wall of the sample container opposite the piston, the elongated member extending through a bore defined in first tension member.

15. The system of claim 14, wherein the elongated member comprises a flanged head and the second tension member defines a recess aligned with and sized to receive the flanged head of the elongated member.

16. A device for testing cement, the device comprising:
a sample container having a flexible tubular member defining a first interior volume and a plurality of tension members defining a second interior volume, the sample container defining an aperture extending between the first interior volume and the second interior volume; and
a piston connected to the sample container;
wherein the tension members are connected to each other such that movement of the piston in a first direction applies compression to a portion of a cement sample in the first interior volume and movement of the piston in a second direction opposite the first direction applies tension to a portion of the cement sample in the second interior volume, and
at least one of the tension members is slidably mounted to an elongated member that is coupled to an end wall of the sample container that defines, at least in part, at least one of the first or second interior volumes.

17. The device of claim 16, wherein the plurality of tension members comprise a first tension member and a second tension member adjacent the first tension member, the second tension member disposed between the piston and first tension member such that movement of the piston in the first direction presses the second tension member towards the first tension member and movement of the piston in the second direction pulls the second tension member away from the first tension member.

18. The device of claim 17, wherein the elongated member is fixed in position relative to the end wall of the sample container opposite the piston, the elongated member extending through a bore defined in first tension member to limit movement of the first tension member towards the piston.

* * * * *

UNITED STATES PATENT AND TRADEMARK OFFICE
CERTIFICATE OF CORRECTION

PATENT NO. : 8,960,013 B2  
APPLICATION NO. : 13/409745  
DATED : February 24, 2015  
INVENTOR(S) : David Leon Meadows et al.

Page 1 of 1

It is certified that error appears in the above-identified patent and that said Letters Patent is hereby corrected as shown below:

Title page, Col. 2 under Attorney, Agent, or Firm, Line 1, please replace "Wustenberg;" with -- Wustenberg, Ph.D.; --

Title page, Col. 2 under Abstract, Line 3, please replace "force a" with -- force in a --

Signed and Sealed this  
Twenty-ninth Day of September, 2015

Michelle K. Lee  
*Director of the United States Patent and Trademark Office*